United States Patent [19]
Collins

[11] Patent Number: 5,203,326
[45] Date of Patent: Apr. 20, 1993

[54] ANTIARRHYTHMIA PACER USING ANTIARRHYTHMIA PACING AND AUTONOMIC NERVE STIMULATION THERAPY

[75] Inventor: Kenneth A. Collins, Neutral Bay, Australia

[73] Assignee: Telectronics Pacing Systems, Inc., Englewood, Colo.

[21] Appl. No.: 809,978

[22] Filed: Dec. 18, 1991

[51] Int. Cl.$^5$ ............................................. A61N 1/362
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,942,534 | 3/1976 | Allen et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,869,252 | 9/1989 | Gilli | 128/419 PG |

OTHER PUBLICATIONS

"Vagal Tuning", Thoracic & Cardiovascular Surgery, vol. 56, #1, Jul 1968, pp. 71–82.

"Implantable Carotid Sinus Nerve Stimulator for Reversal of Hypertension", Surgical Forum. 1966, pp. 123–127.

P. M. Zoll et al., "Ventricular Fibrillation: Treatment and Prevention by External Electric Currents", New England Journal of Medicine, vol. 262, No. 3, pp. 105–112 (Jan. 21, 1960).

E. Sowton et al., "The Suppression of Arrhythmias by Artificial Pacemaking", Lancet, vol. 2, pp. 1098–1100 (Nov. 21, 1964).

J. F. Lopez et al., "Reducing Heart Rate of the Dog by Electrical Stimulation", Circulation Research, vol. 15, pp. 414–429 (Nov. 1964).

J. I. Haft, et al., "Electrical Conversion of Atrial Flutter Without Ventricular Depolarization", Circulation, vols. 33 & 34: Supplement III, pp. 118–119 (Oct. 1966).

N. C. Hunt et al., "Conversion of Supraventricular Tachycardias with Atrial Stimulation—Evidence for Re-entry Mechanisms", Circulation, vol. 38, pp. 1060–1065 (Dec. 1968).

D. P. Zipes et al., "Artificial Atrial and Ventricular Pacing in the Treatment of Arrhythmias", Annals of Internal Medicine, vol. 70, No. 5, pp. 885–896 (May 1969).

J. W. Lister et al., "Treatment of Supraventricular Tachycardias by right Atrial Alternating Current Stimulation", American Journal of Cardiology, vol. 29, pp. 208–212 (Feb. 1972).

(List continued on next page.)

Primary Examiner—William E. Kamm
Assistant Examiner—Jeffrey R. Jastrzab
Attorney, Agent, or Firm—Gottlieb, Rackman & Reisman

[57] ABSTRACT

An antiarrhythmia pacemaker detects the occurrence of an abnormal condition of a patient's heart and, in response, delivers an antiarrhythmia therapy to the patient which includes two components, electrical stimulation of the heart and electrical stimulation of nerves or ganglia in the autonomic nervous system. The antiarrhythmia pacemaker controls electrical stimulation of the heart in terms of timing, frequency, amplitude, duration and other operational parameters, to provide such pacing therapies as antitachycardia pacing, cardioversion and defibrillation. A nerve stimulation electrode, which is driven by a nerve fiber pulse stimulator, stimulates preselected nerve fibers within the patient's autonomic nervous system. An arrhythmia therapy control responds to the detection and confirmation of an abnormal heart condition by controlling and coordinating the heart pulse stimulator and the nerve fiber stimulator to direct performance of a combined heart and nerve stimulation therapy.

30 Claims, 15 Drawing Sheets

OTHER PUBLICATIONS

G. Neumann et al., "A Study of Electrophysiological Changes During Rapid Atrial Burst Stimulation Associated with Re-entry Tachycardias", *Presentations of the 1st European Symposium of Cardiac Pacing,* London, p. 23 (1978).

R. A. J. Spurrell et al., "Pacing Techniques in the Management of Supraventricular Tachycardias", Part 2, *Journal of Electrocardiology,* vol. 9, pp. 89–96 (1979).

M. Akhtar et al., "Electrophysiological Mechanisms for Modification and Abolition of Atrioventricular Junctional Tachycardia with Simultaneous and Sequential Atrial and Ventricular Pacing", *Circulation,* vol. 60, No. 7 pp. 1443–1454 (Dec. 1979).

A. J. Camm et al., "A Microcomputer-Based Tachycardia Termination System-a Preliminary Report", Journal Medical Engineering & Technology, vol. 4, No. 2, pp. 80–83 (Mar. 1980).

P. J. Schwartz, "Sympathetic Imbalance and Cardiac Arrhythmias", *Nervous Control of Vascular Function,* Randall, W. C. ed. pp. 225–252, Oxford University Press (1984).

M. N. Levy et al., "Parasympathetic Control of the Heart", *Nervous Control of Cardiovascular Function,* Randall W. C. ed., pp. 68–94, Oxford University Press (1984).

P. J. Schwartz et al., "The Rational Basis and the Clinical Value of Selective Cardiac Sympathetic Denervation in the Prevention of Malignant Arrhythmias", *European Heat Journal,* vol. 7, Supp. A, pp. 107–118 (1986).

G. Zuanetti et al., "Protective Effect of Vagal Stimulation on Reperfusion Arrhythmias in Cats:", *Circulation Research* vol. 61, (3), pp. 429–435 (1987).

M. Stramba-Badiale et al., "Sympathetic-Parasympathetic Interaction and the Accentuated Antagonism in Conscious Dogs", *American Journal of Physiology,* vol. 260 (2Pt 2): pp. H335–340 (Feb. 1991).

1 SEC SCALE

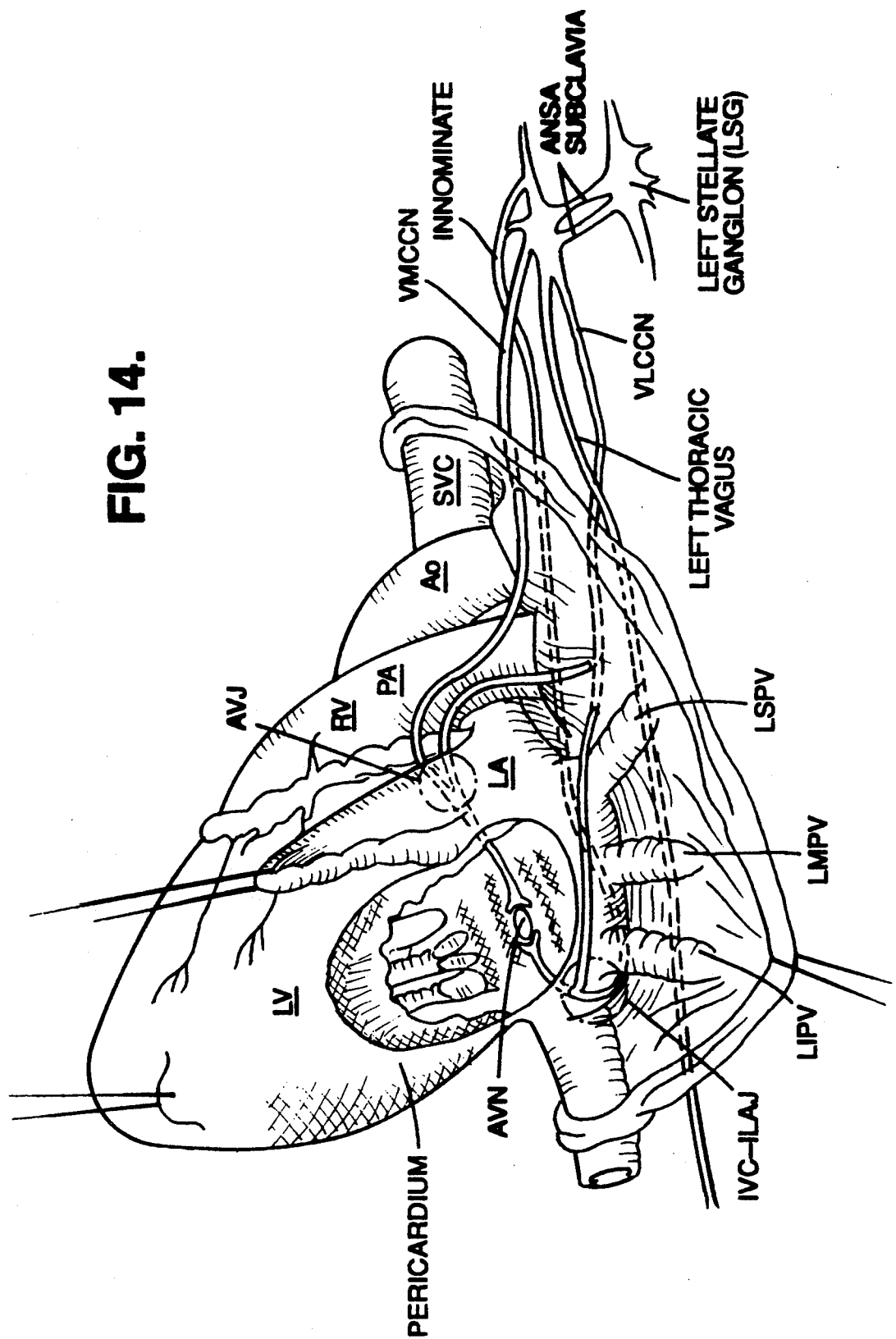

ANTIARRHYTHMIA PACER USING ANTIARRHYTHMIA PACING AND AUTONOMIC NERVE STIMULATION THERAPY

TECHNICAL FIELD

This invention relates to an antiarrhythmia pacing apparatus and its method of operation for detecting abnormalities of a patient's heart and, in response to such detection, administering an antiarrhythmia therapy. More particularly, this invention relates to an antiarrhythmia pacemaker which employs an antiarrhythmia therapy which comprises the coordination, control and generation of stimulation pulses to both the patient's heart and nerve tissue.

BACKGROUND OF THE INVENTION

The ultimate task of an antiarrhythmia pacemaker is to prevent sudden cardiac death. In most cases, sudden cardiac death is caused by ventricular fibrillation, although asystole may occasionally be involved. Heretofore, antiarrhythmia pacemakers have responded to the detection of arrhythmias by generating a therapy involving electrical stimulation of the heart to terminate fibrillation or tachycardia and return the heart's rate to a normal sinus rhythm. These therapies include antitachycardia pacing (ATP), cardioversion and fibrillation. Other mechanisms for altering heart rate are known, such as administration of antiarrhythmic drugs and selective stimulation of the autonomic nervous system.

The antiarrhythmia pacemaker of the present invention utilizes a combination of electrophysiological and autonomic nervous system stimulation to treat cardiac arrhythmias. The autonomic nervous system, which includes sympathetic and parasympathetic nervous systems, is made up of neurons which regulate activity of cardiac muscle, smooth muscle and glands. Rather than functioning by activating and stimulating organs, the autonomic nervous system modifies activities already performed by an innervated organ.

The sympathetic nervous system is the thoracolumbar portion of the autonomic nervous system. Sympathetic stimulation does not cause the heart muscle to contract, but instead increases heart rate, contraction force, velocity at which action potentials travel over nerve fibers and electrical sensitivity of myocardial cells. In response to sympathetic nerve impulses, postganglionic sympathetic fibers release norepinephrine which increases heart rate by stimulating the sino-atrial (S-A) node to fire more rapidly and by facilitating atrioventricular (A-V) conduction.

The parasympathetic nervous system is the craniosacral portion of the autonomic nervous system. In response to parasympathetic impulses, postganglionic parasympathetic fibers release acetycholine to reduce heart rate. Parasympathetic stimulation reduces heart rate by depressing S-A and A-V node activity.

As used herein, the term arrhythmia refers to any fast abnormal rhythm of the heart that is amenable to treatment by electrical discharges. Arrhythmias include supraventricular tachycardia, atrial fibrillation and atrial flutter, ventricular tachycardia, and ventricular flutter and fibrillation. During a tachycardia the heart beats rapidly, with a ventricular rate higher than 100 beats per minute (bpm) and typically above 150 bpm, and an atrial rate as high as 400 bpm.

Tachycardia is often the result of electrical feedback within the heart. A natural beat leads to feedback of an electrical stimulus which prematurely triggers another beat. Several different pacing modalities have been suggested for tachycardia termination, based upon the underlying principle of interposing a stimulated heartbeat shortly before the next premature triggered beat. This disrupts the stability of the feedback loop to allow the heart to revert to sinus rhythm. Such pacing therapy, however, can cause the tachycardia feedback loop to degenerate so that fibrillation ensues.

Ventricular arrhythmias which arise in association with bradycardia occur less frequently when a heart beats at an increased rate. Therefore, patients who are subject to these arrhythmias are commonly treated with chronotropic drugs, such as sympathomimetric amines and atropine. Unfortunately, the results of chronotropic drug therapy are unpredictable. Drugs may aggravate, rather than prevent, arrhythmias. Furthermore, antiarrhythmia drugs do not prevent sudden cardiac death, possibly because the triggering mechanism for fibrillation may be a factor which is not sensitive to the action of these drugs.

One method for preventing ventricular tachycardia and fibrillation in patients with A-V block or bradycardia involves ventricular pacing at normal or overdrive pacing rates (See, e.g., P. M. Zoll, et al., "Ventricular Fibrillation: Treatment and Prevention by External Electric Currents", *New England Journal of Medicine*, Vol. 262, page 105 (1960)). E. Sowton modified this method in "The Suppression of Arrhythmias by Artificial Pacemaking", *Lancet*, Vol. 2, page 1098 (1964), to treat ventricular arrhythmias in patients without A-V block.

D. P. Zipes et al., in "Artificial Atrial and Ventricular Pacing in the Treatment of Arrhythmias", *Annals of Internal Medicine*, Vol. 70, page 885 (1969), found that increasing a patient's heart rate by atrial, rather than ventricular, pacing may confer hemodynamic and electrophysiological advantages by preserving a normal polarization sequence.

R. A. J. Spurrell et al., in "Pacing Techniques in the Management of Supraventricular Tachycardia", Part 2, *Journal of Electrocardiology*, Vol. 9, page 89 (1979), shows that overdrive pacing of both the atrium and ventricle in an eccentric activation sequence prevents and terminates junctional tachycardias (tachyarrhythmias which arise at the atrio-ventricular junction, such as re-entry). Both slow and fast ventricular rates trigger this therapy. Similarly, M. Akhtar et al., in "Electrophysical Mechanisms for Modification and Abolition of Atrioventricular Junctional Tachycardia with Simultaneous and Sequential Atrial and Ventricular Pacing", *Circulation*, Vol. 60, page 1443 (1979), observed that regular simultaneous A-V pacing prevents junctional tachycardias. However, this treatment is not appropriate for long-term junctional tachycardia prevention because of the risk of atrial premature beats or atrial tachycardias triggering improperly high ventricular rates, leading to harmful ventricular arrhythmias.

Continuous high rate atrial pacing may control supraventricular or atrial tachycardias, thereby preventing dangerous ventricular arrhythmias, because atrial pacing at a rate higher than a tachycardia rate may block atrio-ventricular transmission to reduce the ventricular rate. J. W. Lister et al., in "Treatment of Supraventricular Tachycardias by Right Alternating Current Stimulation", *American Journal of Cardiology*, Vol. 29, page 208 (1972), prevented aggravation of atrial tachycardia into atrial fibrillation in this manner and found that ventricular rate in response to atrial fibrillation was less than the originally occurring atrial tachycardia rate. Unfortunately, continuous high rate atrial pacing is limited to short-term use because fluctuations in autonomic tone may cause intermittently higher A-V conduction rates and transmit the atrial high rate directly to the ventricle, risking dangerous ventricular arrhythmias.

J. F. Lopez et al., in "Reducing the Heart Rate in the Dog by Electrical Stimulation", *Circulation Research*, Vol. 15, page 414 (1964), slows atrial arrhythmias using atrial paired and coupled stimulation, stimulation by two pulses of short duration in which the first pulse stimulates the atrium and the second pulse occurs at a time when the A-V junction is refractory, thus preventing a ventricular response. Paired and coupled stimulation has also been applied in the ventricle, with inconsistent results, to control heart rate in supraventricular arrhythmia, atrial fibrillation and persistent ventricular tachycardia patients.

These techniques effectively prevent tachycardias for short periods of time under the direct supervision of a health care professional. However, the risk of initiating or aggravating dangerous arrhythmias due to the inability to adapt to varied physiological circumstances renders these methods and devices inappropriately dangerous for long-term, automatic use. What is needed is a technique for long-term arrhythmia prevention in an automatic, implantable system.

J. I. Haft et al., in "Electrical Conversion of Atrial Flutter without Ventricular Depolarization", *Circulation*, Vol. 34: III, page 118 (1966), terminated atrial tachycardia and atrial flutter using rapid repetitive atrial stimulation. Results of this therapy were inconsistent, with a high incidence of atrial fibrillation, but were improved considerably by augmenting pacing with the application of antiarrhythmic agents.

G. Neumann et al., in "A Study of Electrophysiological Changes During Rapid Atrial Burst Stimulation Associated with Reentry Tachycardias", *Presentations of the 1st European Symposium of Cardiac Pacing*, London, page 23 (1978), improved upon the technique of rapid repetitive stimulation by devising a pacemaker in which the initial interval between an atrial event and delivery of a burst was required to exceed 250 ms, thus avoiding early stimulation in the vulnerable phase with its risk of initiating atrial fibrillation. Another solution to this problem is termed "autodecremental" pacing in which the initial coupling interval of a burst is delivered very late in the tachycardia cycle but is followed by a gradual acceleration of the pacing rate up to a limit determined by the pacing interval. (See, e.g., A. J. Camm et al., "A Microcomputer-Based Tachycardia Termination System—A Preliminary Report", in *Journal Medical Engineering Technical*, Vol. 4, page 80 (1980)). Long-term results using rapid repetitive stimulation techniques are disappointing due to provocation of atrial fibrillation.

Underdrive pacing, using critically coupled premature beats, is an alternative to rapid repetitive stimulation for the termination of arrhythmias. N. C. Hunt et al., in "Conversion of Supraventricular Tachycardias with Atrial Stimulation—Evidence for Reentry Mechanism", *Circulation*, Vol. 38, page 1060 (1968), used underdrive pacing in which, sooner or later by random competition, an appropriately times stimulus occurs and terminates a tachycardia. Unfortunately, underdrive pacing is usually ineffective if a tachycardia rate exceeds 160 beats per minute. Since antitachycardia therapy is commonly not activated until tachycardia rate is above about 140 beats per minute, there is only a narrow range of tachycardia rates and a small proportion of tachycardias which automatic underdrive pacing may assist.

Most recently, pacing by critically timed premature beat pulses has been employed to terminate tachycardias. A pacemaker scans the heart's diastolic period of the tachycardia cycle with one or more stimuli to provide critical timing.

All of these cardiac arrhythmias treatment techniques involve delivery of stimulation pulses to cardiac tissue. Cardiovascular system performance is also affected by techniques which alter autonomic nervous system function. Modified autonomic nervous system activity, by sectioning or cold blocking of nerve impulses or by autonomic nerve stimulation, has been employed to alter heart rate. For example, P. J. Schwartz et al. in "Sympathetic Imbalance and Cardiac Arrhythmias", from *Nervous Control of Vascular Function*, Randall WC ed., Oxford University Press (1984), expresses that electrical stimulation of sympathetic nerves lowers the ventricular fibrillation threshold and increases vulnerability to fibrillation. In contrast, electrical stimulation of parasympathetic nerves raises the ventricular fibrillation threshold by depressing action of sympathetic nerves. Note that if sympathetic activity is low already, no change can be expected by deactivating sympathetic nerves.

M. Stramba-Badiale et al. found that parasympathetic nervous system stimulation by vagus nerve excitation is advantageous for treating arrhythmias, in "Sympathetic-Parasympathetic Interaction and Accentuated Antagonism in Conscious Dogs", *American Journal of Physiology*, Vol. 260 (2Pt 2): pages H335-340 (Feb 91). Vagal activity contributes to cardiac electrical stability. Conversely, a decreased vagal tone and reflex is associated with a heightened risk of sudden cardiac death.

G. Zuanetti et al. in "Protective Effect of Vagal Stimulation on Reperfusion Arrhythmias in Cats", *Circulation Research* Vol. 61(3), pages 429-435 (1987) found that combined bradycardia pacing and vagal stimulation protected against sustained ventricular tachycardia, whereas pacing alone aggravated or initiated arrhythmias. Zuanetti did not attempt nerve stimulation in combination with arrhythmia therapy, such as antitachycardia pacing, cardioversion or defibrillation.

These prior art systems either, in the first instance, employ antiarrhythmia pacing, cardioversion or defibrillation in response to the detection of a rapid cardiac rhythm to terminate such an arrhythmia; or, alternatively, utilize constant long-term autonomic nervous system modification to prevent arrhythmias. The prior art does not appear to disclose an apparatus or method for detecting a cardiac abnormality, including precursors to arrhythmias, tachyarrhythmias or fibrillation and, in response to such detection, applying a combined therapy of antiarrhythmia pacing and autonomic nerve stimulation.

BRIEF SUMMARY OF THE INVENTION

In accordance with the principles of the present invention, an antiarrhythmia pacemaker detects and confirms an occurrence of an abnormal condition of a patient's heart and, in response, delivers an antiarrhythmia therapy. This therapy includes two components, electrical stimulation of the heart and electrical stimulation of autonomic nerves or ganglia.

The antiarrhythmia pacemaker includes a heart pulse stimulating means which generates and delivers electrical stimulation pulses to the heart. The pacemaker controls pulse timing, frequency, amplitude, duration and other operational parameters to selectively generate pacing therapies such as antitachycardia pacing, cardioversion and defibrillation.

The antiarrhythmia pacemaker also includes a nerve stimulation electrode which is adapted to be placed in electrical contact with preselected nerve fibers within the patient's autonomic nervous system. The nerve stimulation electrode is electrically coupled to a nerve fiber pulse stimulating means which generates and delivers nerve tissue stimulation pulses to the electrodes for the purpose of stimulating these preselected nerve fibers.

An arrhythmia therapy control means responds to detection and confirmation of an abnormal condition of a patient's heart by controlling and coordinating the operation of the heart pulse stimulating means and the nerve fiber stimulating means to direct performance of a combined heart pacing and nerve stimulation therapy.

The antiarrhythmia pacemaker is adapted to activate the parasympathetic nervous system by means of electrical stimulation of autonomic nerves or ganglia to prevent or treat malignant arrhythmias. When the patient's afferent sympathetic nervous system activity increases, due to physiological stress from reflex mechanisms or as a reaction to pain or fear, the antiarrhythmia pacemaker senses this occurrence by analyzing one or more physiological signals. The pacemaker initiates and coordinates a therapy involving antiarrhythmia pacing therapy and vagal nerve stimulation therapy. Vagal nerve stimulation increases vagal tone, which produces antiarrhythmic effects, decreasing the risk of ventricular fibrillation.

Combined cardiac electrical stimulation and autonomic nervous stimulation therapy is most advantageous in an antiarrhythmia pacemaker which detects and confirms various abnormal conditions of the heart. These conditions include existence of arrhythmia precursors, in addition to tachycardia and fibrillation. Prior art implantable antitachycardia pacemakers commonly only detect and initiate therapy upon the occurrence of tachycardia and fibrillation alone.

P. J. Schwartz et al. in "The Rational Basis and the Clinical Value of Cardiac Sympathetic Denervation in the Prevention of Malignant Arrhythmias", *European Heart Journal*, V7, Supp A, pp107-118 (1986), relates that analysis of Holter recordings from patients who died of sudden cardiac death shows, in a significant number of cases, the onset of ventricular fibrillation is closely preceded by T wave ST segment changes related to myocardial ischemia, even if the myocardial ischemia episode has a very brief duration. Sympathetic activation from reflex mechanisms and as a reaction to pain or fear is a primary cause of the electrophysiological derangements which accompany the onset of acute myocardial ischemia. Dangerous arrhythmias arise from the interaction between acute myocardial ischemia and sympathetic hyperactivity. This dangerous situation is not alleviated by standard medical intervention since antiarrhythmic drugs do not suppress this interaction.

The present invention detects precursors to cardiac arrhythmia and initiates a therapy including autonomic nervous system stimulation and antiarrhythmia pacing therapy to directly inhibit sympathetic action and break the interaction between myocardial ischemia and sympathetic hyperactivity.

The antiarrhythmia pacemaker of the present invention detects the earliest occurring heart abnormalities, from arrhythmia precursors to tachycardias to fibrillation, allowing early therapeutic intervention to prevent increasingly dangerous heart conditions.

In patients with recurrent arrhythmias, the initial approach of the antiarrhythmia pacemaker is prevention, including parasympathetic nerve stimulation to inhibit provocative sympathetic activity and pacing stimulation to the heart to correct underlying potentially-reversible conduction abnormalities.

If arrhythmias cannot be prevented, the antiarrhythmia pacemaker acts, through parasympathetic stimulation, to reduce the heart's ventricular response during arrhythmia. Vagal stimulation during acute myocardial ischemia has the known propensity to prevent ventricular fibrillation. Furthermore, vagal activation is effective to reproducibly terminate episodes of ventricular tachycardia.

Upon a tachycardia's occurrence, the antiarrhythmia pacemaker provides an interventional therapy which increases vagal tone by directly stimulating the parasympathetic nervous system. Interventions which increase vagal tone provide the simplest methods for terminating tachycardias. Interventions which are known in the prior art include manual and manipulative therapies such as the Valsalva maneuver, the 'diving' reflex, carotid sinus massage and eyeball pressure.

The antiarrhythmia pacemaker provides flexible treatment for various heart problems and symptoms.

BRIEF DESCRIPTION OF THE DRAWINGS

Further objects, features and advantages of the invention will become apparent upon consideration of the following description, taken in conjunction with the accompanying drawings, in which:

FIGS. 13A and 13B illustrate a comparison of cardiac and neural stimulation timing as controlled by the antiarrhythmia pacemaker of the present invention, in which FIG. 13A illustrates a burst of nerve stimulation pulses and FIG. 13B illustrates a single pulse;

FIG. 14 depicts a left lateral view of the heart illustrating sympathetic and parasympathetic autonomic innervation of the A-V nodal region of a canine heart;

DETAILED DESCRIPTION OF THE INVENTION

Figure 1:
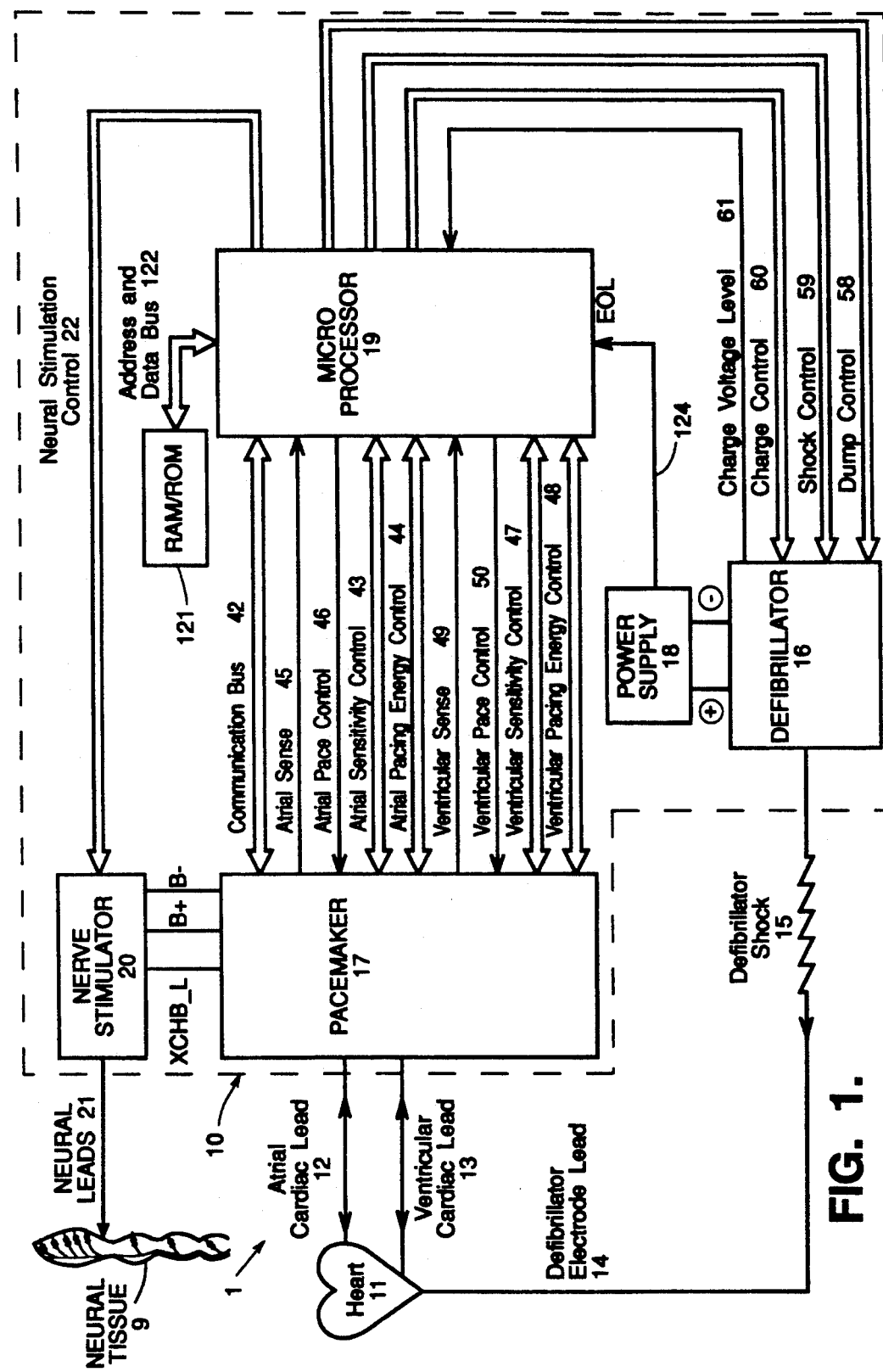
FIG. 1 is a block diagram of an implanted, rate-responsive, dual chamber arrhythmia control system (ACS) in accordance with the present invention.

Referring to FIG. 1, there is depicted a block diagram of an arrhythmia control system 1. System 1 is designed to be implantable in a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium, and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to pacemaker 17, nerve stimulator 20 and defibrillator 16; and a power supply 18 for the provision of a reliable voltage level to pacemaker 17, microprocessor 19, nerve stimulator 20 and defibrillator 16 by suitable electrical conductors (not shown). Nerve stimulator 20 generates electrical pulses on neural leads 21 for stimulating neural tissue 9, such as nerves and ganglia, according to timed control signals from microprocessor 19 communicated via neural stimulation control bus 22. Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

Microprocessor 19 is connected to a random access memory/read only memory (RAM/ROM) unit 121 by an address and data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48. Microprocessor 19 transmits control signals, according to the description below, over neural stimulation control bus 22 to the nerve stimulator 20. As also more fully described below, microprocessor 19 is connected to defibrillator 16 by a charge voltage level line 61, a charge control bus 60, a shock control bus 59, and a dump control bus 58.

Figure 2:
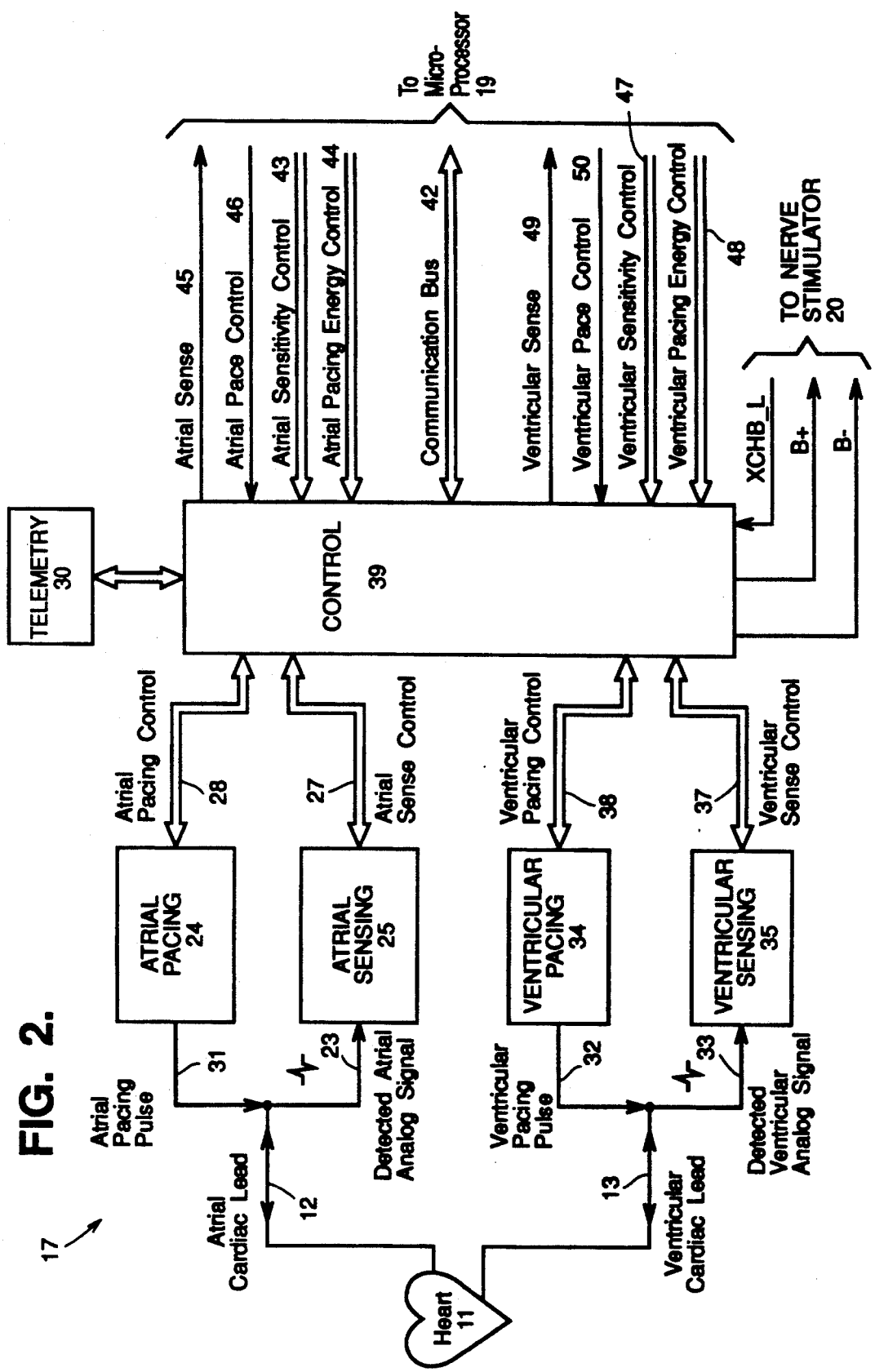
FIG. 2 is a block diagram of a pacemaker utilized in the system of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to be delivered to the heart via atrial pacing pulse lead 31 and atrial cardiac lead 12, and via ventricular pacing pulse lead 32 and ventricular cardiac lead 13, respectively. The atrial and ventricular pacing energy control inputs determine the respective magnitudes of the pacing pulse energy so delivered. The operation of the logic which changes the pulse energy is described in greater detail in U.S. Pat. No. 4,869,252 to Norma Louise Gilli, issued Sep. 26, 1989, and entitled "Apparatus And Method For Controlling Pulse Energy In Antitachyarrhythmia And Bradycardia Pacing Devices," which description is incorporated herein by reference.

Telemetry circuit 30 provides a bidirectional link between control block 39 of pacemaker 17 and an external device such as a programmer. It allows data such as the operating parameters to be read from or altered in the implanted module 10.

Figure 3:
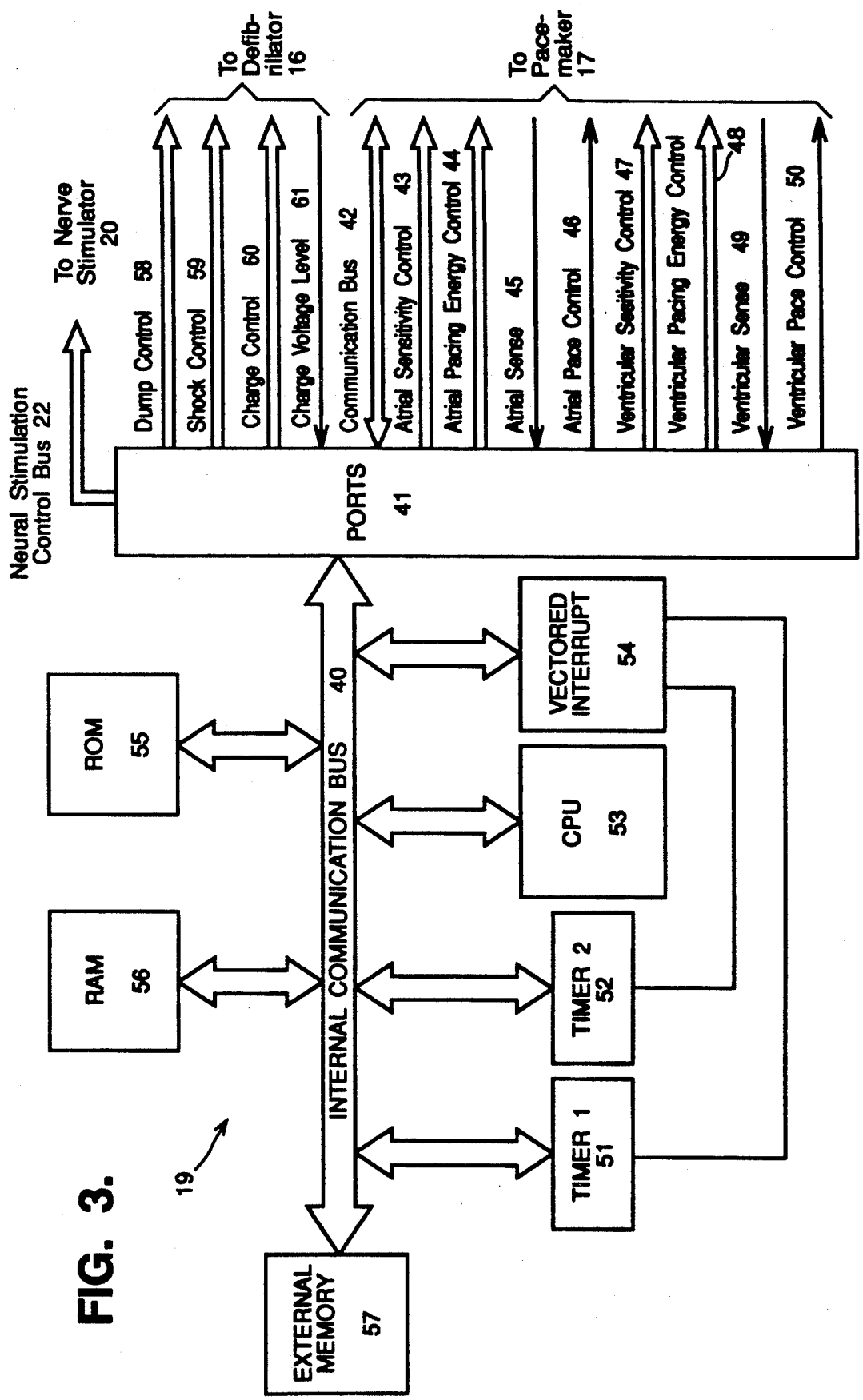
FIG. 3 is a block diagram of a microprocessor utilized in the system of FIG. 1.

Referring to FIG. 3, microprocessor 19 comprises two 16-bit timers 51 and 52, a CPU 53, a vectored interrupts block 54, a ROM 55, a RAM 56, an external memory 57, a ports block 41 and an internal communications bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic flow diagrams of FIG. 6 and FIG. 11, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communication bus 42 serves to provide signals indicative of such control to microprocessor 19. Thus, it is also possible for an external programmer to control operation of the nerve stimulator 20 and the defibrillator 16 by means of signals provided to microprocessor 19.

Appropriate telemetry commands may cause telemetry circuit 30 to transmit data to the external programmer. Data stored is read out, by microprocessor 19, on to communication bus 42, through control block 39 in pacemaker 17, and into telemetry circuit 30 for transmission to the external programmer by a transmitter in telemetry circuit 30.

Microprocessor 19 receives various status and/or control inputs from the pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, the shock control on bus 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. In addition, the microprocessor 19 controls all aspects of neural stimulation, as will be described in detail below, by formulating control signals and transmitting these signals over the neural stimulation control bus 22 to nerve stimulator 20. Charge voltage level line 61 provides a digital signal representative of charge voltage from an analog-to-digital converter within defibrillator 16, thus providing a feedback loop which assures that a shock of proper energy level is delivered by defibrillator 16.

Figure 4:
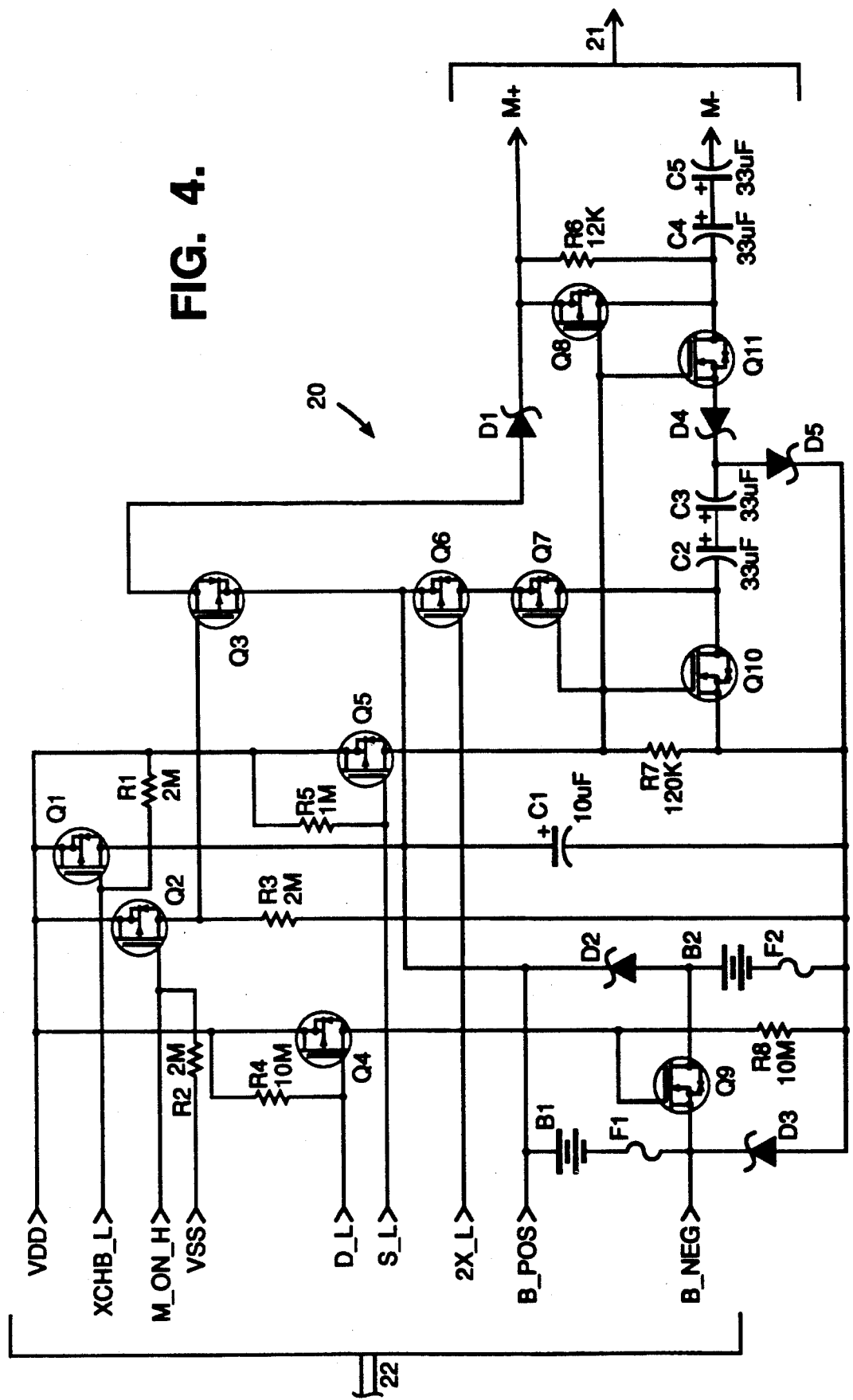
FIG. 4 depicts a circuit schematic of a nerve stimulator utilized in the system of FIG. 1.

Referring to FIG. 4, the nerve stimulator 20 receives input signals from microprocessor 19 over the neural input stimulation control bus 22. These signals include power (VDD), which is typically an amplitude of 2.8V, and ground reference (VSS) as well as control signals S—L, 2X—L, D—L, XCHB—L and M—ON—H. The pacemaker 17 supplies battery power B—POS and B—NEG which provides energy for biphasic neural stimulation. In the preferred embodiment of the present invention, the B—POS amplitude is about 3V. The battery voltages B—POS and B—NEG are floating with respect to circuit power VDD to prevent variations in circuit energy during different parts of the cardiac cycle caused by inconsistent demands on the battery from the pacing pulse and neural stimulation pulse generation circuits.

XCHB—L, a cross channel blanking control signal, from the microprocessor, is also supplied to a sense blanking input of the pacemaker 17 to disable pacemaker sensing during generation of a neural stimulation pulse. This prevents the pacemaker 17 from incorrectly classifying a neural stimulation pulse as an episode of intrinsic cardiac activity.

The circuit of FIG. 4, in response to codes written from the microprocessor, produces biphasic neural stimulation pulses on the neural leads 21, M+ and M—. All characteristics of the neural stimulation pulses: the timing, frequency, burst duration, amplitude, pulse width, and pulse morphology, are determined by the microprocessor. FIG. 4 circuitry merely responds to these input codes by producing a particular amplitude and polarity signal on the M+ and M— leads. In this manner, the microprocessor generates the characteristics of the neural stimulation pulses according to the timing of codes written to the neural stimulation control bus 22.

Figure 5:
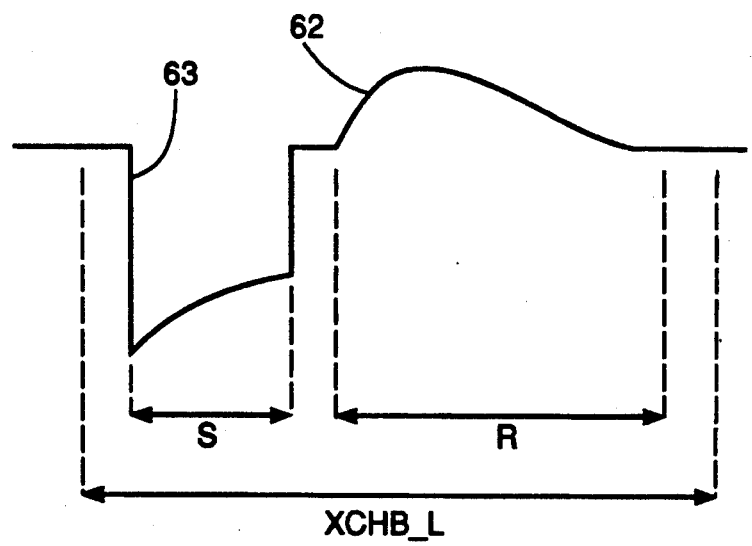
FIG. 5 depicts the form of a biphasic neural stimulation pulse generated by the circuit of FIG. 4.

Input signal lines S—L, M—ON—H and XCHB—L contain nerve pulse enable and polarity control signals which are dynamic in the sense that the microprocessor 19 writes and times the codes written to these lines to produce a particular amplitude for a predetermined duration. The microprocessor enables the circuit of FIG. 4 to produce an output on one or the other of leads M+ and M— by setting input signal line M—ON—H to 1 which, by means of control by p-channel switching field effect transistor Q3, applies either B—POS or B—NEG battery power to the corresponding leads M+ and M—, depending on the signal on input signal line S—L. The microprocessor controls the stimulus pulse timing and width by setting a signal on input signal line S—L for a predetermined time and duration. When the microprocessor writes a 0 value to input signal line S—L, while a 1 value is on input signal line M—ON—H, the outputs of p-channel switching field effect transistors Q7 and Q8 are enabled to enable the M+ lead, and the outputs of n-channel switching field effect transistors Q10 and Q11 are disabled to disable the M— lead, producing a positive polarity output pulse, having a duration R, as shown at 62 in FIG. 5. Alternatively, the microprocessor may write a 1 value to line S—L to disable field effect transistors Q7 and Q8 and enable transistors Q10 and Q11 to produce a negative polarity output pulse, having a duration S, as shown at 63 in FIG. 5. If the value applied to input signal line M—ON—H is 0, neither lead M+ nor lead M— are energized and the nerve stimulator does not produce a pulse. If the value on input signal line M—ON—H is set to 1 and the value on line S—L is set to 0, lead M+ is energized and the nerve stimulator produces a positive polarity pulse 62, as shown in FIG. 5. The duration R is a programmable parameter for the microprocessor. If the value on line M—ON—H is set to 1 and the value on line S—L is set to 1, lead M— is energized and the nerve stimulator produces a negative polarity pulse 63, having the duration S of FIG. 5. Stimulus duration S is a programmable parameter for the microprocessor. The microprocessor controls line XCHB—L to set the timing and duration of the sense blanking input of the pacemaker 17 to disable pacemaker sensing during generation of a neural stimulation pulse. Cross channel blanking duration may be a programmable parameter for the microprocessor.

Input signal lines D__L and 2X__L contain nerve pulse amplitude controls which are static in the sense that the microprocessor 19 writes them, at most, only once per cycle. Normally, the microprocessor only writes amplitude control signals upon reprogramming, via telemetry, by an external communicating device. Line D__L is utilized as a battery voltage doubler. Line 2X__L is utilized as a stimulus voltage doubler. Thus, lines D__L and 2X__L remain at the same settings throughout numerous cardiac cycles, while the nerve stimulation pulse that is generated has a negative, positive or zero polarity. When the microprocessor sets line D__L to 1 ("on"), the n-channel switching field effect transistor Q9 enables doubling of the battery voltage. In a similar manner (but with an opposite polarity), when the microprocessor sets line 2X__L to 0 ("on"), the p-channel switching field effect transistor Q9 enables doubling of the stimulus voltage. Therefore, when the microprocessor sets line D__L "off" (0) and 2X__L "off" (1), the amplitude of the nerve stimulation pulse is equal to the battery voltage, 3V in the preferred embodiment of the invention. When the microprocessor sets D__L "on" (1) and 2X__L "off" (1), the amplitude of the nerve stimulation pulse is equal to twice the battery voltage (6V). When the microprocessor sets D__L "on" (1) and 2X__L "on" (0), the amplitude of the nerve stimulation pulse is equal to four times the battery voltage (12V).

Referring again to FIG. 1, when the microprocessor 19 determines that nerve stimulation is appropriate, it works in conjunction with the nerve stimulator 20 to produce pulses or bursts of pulses, which are applied to the neural tissue 9. The microprocessor may time these pulses or bursts of pulses with respect to intrinsic or paced cardiac activity which is sensed or generated, respectively, by the pacemaker 17. This mode of nerve stimulation is termed "synchronous" neural stimulation. Alternatively, the microprocessor 19 may time the pulses or bursts of pulses according to the operations of an internal timer, wherein the stimulation occurs asynchronously with respect to individual cardiac events.

According to "synchronous" programming of the microprocessor 19, when the pacemaker 17 detects either a natural atrial or a natural ventricular intrinsic event it will send a signal to the microprocessor 19 via atrial sense line 45 or ventricular sense line 49. The microprocessor 19 may be programmed to respond to such a signal by generating neural stimulation. Alternatively, in the event that the patient's natural heart rate falls below a predetermined rate, then the microprocessor 19 will send an atrial pace control signal on line 46, a ventricular pace control signal on line 50, or both signals to the pacemaker 17 to generate a pacing pulse to the heart. In addition, the microprocessor may be programmed to trigger neural stimulation after such a pacing event. Programming of synchronous operation of the nerve stimulator includes the specification of a synchronization ratio which determines the ratio of cardiac events for each nerve stimulation burst. The microprocessor 19 resets a cardiac event counter with each initiation of a nerve stimulation burst and increments the counter with each subsequent cardiac event. For each nerve stimulation burst, the microprocessor 19 waits a predetermined and programmed delay interval before initiating the burst.

Other programmed parameters which may be utilized are an interpulse interval, the stimulus duration, the recharge duration, the cross-channel blanking duration and a maximum neurostimulation rate. All or some of these parameters may have preprogrammed sets of values which depend on the rate at which the heart is beating. An interpulse interval determines the time intervals between each individual pulse within a burst of pulses. A burst frequency is the reciprocal of the interpulse interval. The maximum neurostimulation rate is an upper rate boundary of synchronization of cardiac and neurostimulation activity. Upon a cardiac event occurring at cardiac rates faster than the maximum neurostimulation rate, the microprocessor will fail to generate nerve stimulation but will, instead, stimulate the nerve based upon triggering by the next subsequent cardiac event.

The antiarrhythmia pacemaker of the present invention monitors activity of the heart to determine when and how to deliver an antiarrhythmia therapy. The flow chart of FIG. 6 defines one example of arrhythmia detection, confirmation and classification operations, performed by a microprocessor, which may be employed by the antiarrhythmia pacemaker of the present invention. The microprocessor 19 of FIG. 1 is programmed to respond to atrial sense signals on line 45 and ventricular sense signals on line 49 from the pacemaker 17. For some or all cardiac cycles, the microprocessor may measure a time interval associated with that cardiac cycle. The program in the microprocessor may define a cardiac cycle as an atrial cycle interval (P wave to P wave) or a ventricular cycle interval (R wave to R wave). Furthermore, interval timing may relate to stimulated cardiac events as well as to intrinsic cardiac events.

Figure 6:
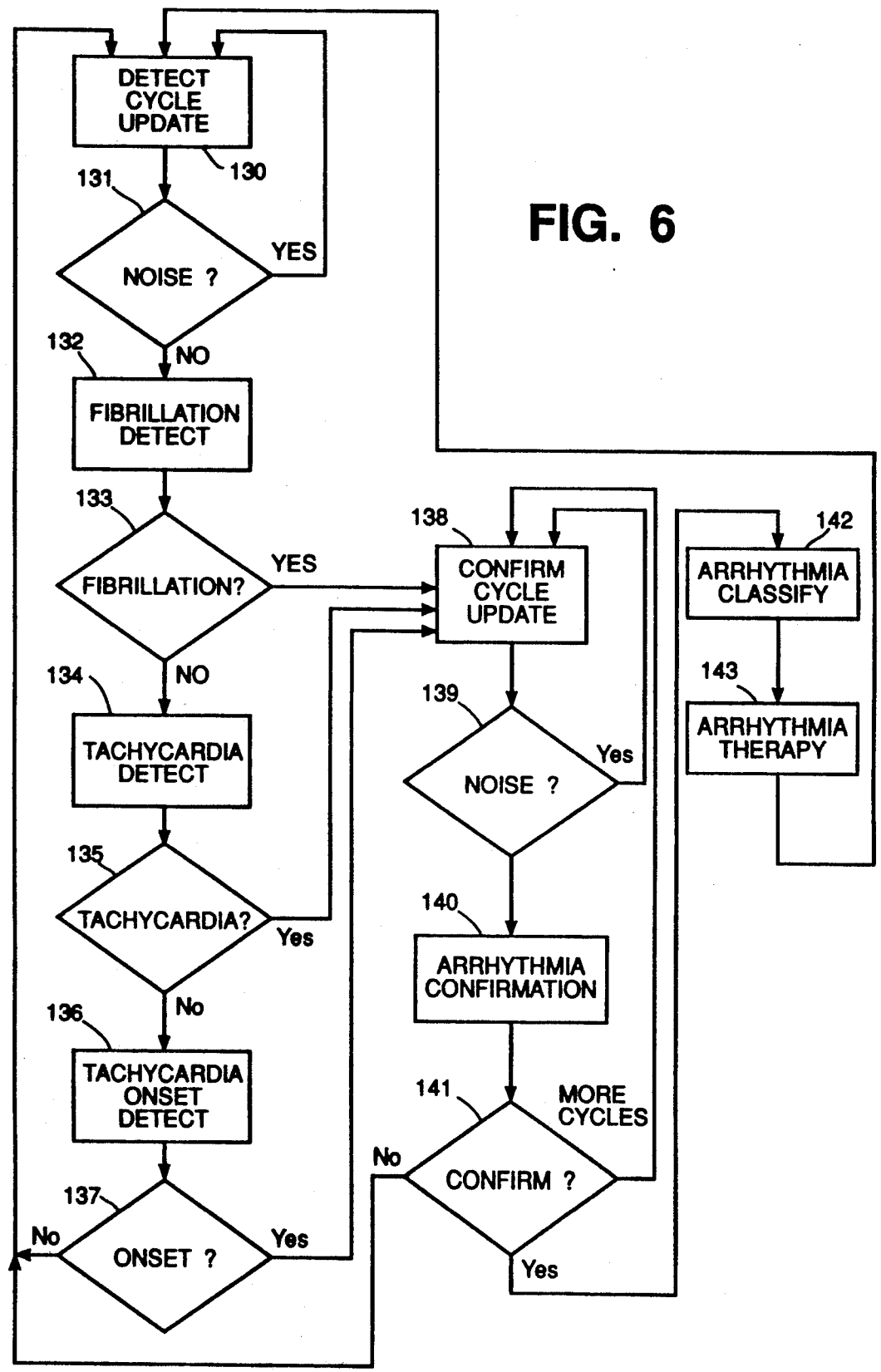
FIG. 6 is a flow chart setting forth the operations of arrhythmia detection, confirmation and classification.

Referring to FIG. 6, microprocessor 19 first performs arrhythmia detection. In a detect cycle update 130 operation, the microprocessor measures the time interval associated with the present cardiac cycle. The microprocessor may discard interval information for a particular cardiac cycle based on the duration of an interval so as to ignore signals due to noise or artifacts, as controlled by the detect cycle noise 131 logic operation. The resulting interval information as well as a log of information concerning the recent history of interval information is stored by the microprocessor in RAM memory 121 (FIG. 1) and used to detect, confirm and classify arrhythmias. During arrhythmia detection, unless a cardiac cycle is characterized as a noise cycle, each time the microprocessor updates the interval duration and interval history memories in block 130, it begins to perform arrhythmia detection, beginning with fibrillation detection 132 operation. Fibrillation detection 132 operation distinguishes tachyarrhythmias with very short intervals by comparing the current interval duration to a predetermined short interval, called a fibrillation detection interval, which is considered to be indicative of fibrillation (for example, 250 ms). However, the microprocessor does not detect an arrhythmia based on only one cardiac cycle. Instead, an X out of Y detection criterion is used to define an arrhythmia, in which a criterion is met only when at least X of the last Y cardiac cycles have cycle intervals shorter than the defined interval. For example, fibrillation detection may require that 8 of the last 10 intervals be shorter than 250 ms. If so, a fibrillation detect 133 logic operation initiates arrhythmia confirmation, beginning with a confirm cycle update 138 operation. If not, the microprocessor performs a tachycardia detection 134 operation.

Tachycardia detection 134 operation discerns tachycardias in the same manner as fibrillation detection 132 operation described above, by comparing the current cardiac cycle length with a predetermined limit and by monitoring the history of cardiac cycle lengths with respect to this comparison. The cycle length limit is called a tachycardia detection interval. It is programmable to a duration ranging from 200 to 600 ms. The X of Y detection criterion for tachycardia detection is also programmable. Common criteria may be 8 out of 10, 12 out of 15 or 16 out of 20. If the X of Y criterion is met, a tachycardia detect 135 logic operation initiates arrhythmia confirmation, beginning with the confirm cycle update 138 operation. If not, the microprocessor performs a tachycardia onset detection 136 operation.

Tachycardia onset detection 136 operation recognizes a sudden and sustained decrease in interval duration to indicate the onset of a tachyarrhythmia. It incorporates two detection methods, the X of Y criterion to ensure that the decrease in interval length is sustained and a change of interval detector which checks for a sudden change in interval length. The change of interval detector employs a predetermined and programmable delta function. Delta is the amount by which the intervals must decrease at onset to satisfy the change of interval detector. The cycle length limit is programmable and called an onset detection interval. The range of onset detection intervals is, like the tachycardia detection interval, from 200 to 600 ms. However, the onset detection interval must be programmed to an interval length longer than the tachycardia detection interval. The X of Y detection criterion for tachycardia onset detection is also programmable.

The detect cycle update 130 operation performs two averaging operations for usage by the change of interval detector. When the cardiac rhythm is stable and slow, detect cycle update averages cardiac cycle intervals to obtain a normal sinus rhythm interval. This averaging occurs when cardiac cycle intervals are longer than the onset detection interval for more than a predetermined number of consecutive cardiac cycles. The detect cycle update 130 operation also performs a short-term average of a predetermined number of the most recent cardiac cycles (for example, 2 cycles). The tachycardia onset detector 136, discerns a change of interval when the short-term average interval is shorter than the normal sinus rhythm interval less the predetermined and programmed delta interval. If the change of interval and onset X of Y criterion is met, an onset detect 137 logic operation initiates arrhythmia confirmation, beginning with the confirm cycle update 138 operation. If not, the microprocessor has not detected an arrhythmia and operation control returns to the detect cycle update 130 operation.

The confirm cycle update 138 operation is analogous to the detect cycle update 130 operation. The microprocessor measures the time interval associated with the present cardiac cycle, discards interval information for noisy cardiac cycles (under the control of the confirm cycle noise 139 logic operation), and logs interval length and interval length history information.

An arrhythmia confirmation 140 operation confirms the tachycardia pacing, cardioversion or defibrillation therapy. Like the arrhythmia detection operations 132, 134 and 136, arrhythmia confirmation uses an X out of Y criterion which compares a history of intervals compiled in the confirmation cycle update 138 operation with respect to a tachycardia confirmation interval. The value of the tachycardia confirmation interval depends on the arrhythmia detector which determined the presence of an arrhythmia. If the arrhythmia was detected by the tachycardia onset detector, the tachycardia confirmation interval is set to the normal sinus rhythm interval determined by the detect cycle update 130 operation less one-half the predetermined and programmed delta interval. If the arrhythmia was detected by the fibrillation or tachycardia detector, the tachycardia confirmation interval is set to the tachycardia detection interval. The X out of Y criterion is predetermined and may be programmed. In a confirmation logic 141 operation, if the X out of Y criterion is met, the pacemaker performs an arrhythmia classification 142 operation. If the criterion is not met, the pacemaker again monitors for arrhythmia detection in the detect cycle update 130 operation. If more cycles are required to determine whether the X of Y criterion is met, control returns to the confirm cycle update 138 operation.

After confirmation of tachyarrhythmia and before delivering therapy, the arrhythmia classification 142 operation classifies the tachyarrhythmia to determine the therapy or therapies to be used in treating the tachyarrhythmia. Classification is based on an X out of Y criterion applied to the cardiac cycle intervals which were monitored in confirmation cycle update 138 operation. These cycle intervals are compared to two predetermined and programmable intervals—a minimum tachycardia cycle length for antitachycardia pacing ($MinTCL_{ATP}$) and a maximum tachycardia cycle length for defibrillation ($MaxTCL_{dfib}$). For arrhythmias with detected intervals shorter than $MinTCL_{ATP}$, antitachycardia pacing is ineffective. For arrhythmias with detected intervals shorter than $MaxTCL_{dfib}$, that patient is considered to be hemodynamically compromised by the arrhythmia and therefore requires defibrillation shock therapy. So if the detected intervals are longer than $MinTCL_{ATP}$, the microprocessor initiates antitachycardia pacing in an arrhythmia therapy 143 operation. (Note that arrhythmia has been confirmed at this point.) If the detected intervals are shorter than $MinTCL_{ATP}$ but longer than $MaxTCL_{dfib}$, the microprocessor initiates antitachycardia pacing in the arrhythmia therapy 143 operation, but will also use defibrillation if antitachycardia pacing is not successful. If the detected intervals are shorter than $MaxTCL_{dfib}$, then the microprocessor initiates defibrillation in the arrhythmia therapy 143 operation. The arrhythmia therapy 143 operation is discussed in detail hereinafter. Following the arrhythmia therapy 143 operation, the pacemaker returns to arrhythmia detection operation in detect cycle update block 130.

Other embodiments of the antitachycardia pacemaker of the present invention may employ other means for detecting the occurrence of arrhythmia episodes, some of which involve the usage of physiological and metabolic sensors. In this regard, reference may be made to U.S. patent application Ser. No. 654,930, entitled "APPARATUS AND METHOD FOR DETECTING ABNORMAL CARDIAC RHYTHMS IN DUAL CHAMBER ARRHYTHMIA CONTROL SYSTEM", filed on Feb. 13, 1991, in the names of Tibor A. Nappholz et al., and to U.S. patent application Ser. No. 665,842, entitled "APPARATUS AND METHOD FOR DETECTING ABNORMAL CARDIAC RHYTHMS USING AN ULTRASOUND SENSOR IN AN ARRHYTHMIA CONTROL SYSTEM", filed on Mar. 8, 1991, in the names of Tibor A. Nappholz et al., both of which are assigned to the assignee of the present invention. Reference may also be made to U.S. patent application Ser. No. 667,316, entitled "APPARATUS AND METHOD FOR DETECTING ABNORMAL CARDIAC RHYTHMS USING EVOKED POTENTIAL MEASUREMENTS IN AN ARRHYTHMIA CONTROL SYSTEM", filed on Mar. 8, 1991, in the names of Tibor A. Nappholz et al., and to U.S. patent application Ser. No. 738,184, entitled "DETECTION OF CARDIAC ARRHYTHMIAS USING CORRELATION OF CARDIAC ELECTRICAL SIGNALS AND TEMPORAL DATA COMPRESSION", filed on Jul. 29, 1991, in the names of Bruce M. Steinhaus et al., both of which are assigned to the assignee of the present invention.

In addition to performing an antiarrhythmia therapy in response to the detection of arrhythmias, the antiarrhythmia pacemaker of the present invention also performs a therapy upon the detection of arrhythmia precursors.

Figure 7A:
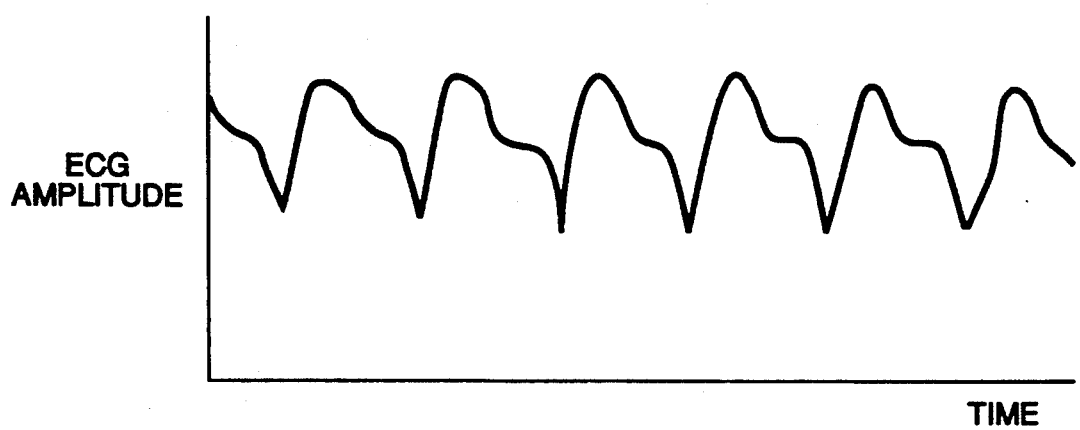
FIGS. 7A-7C are illustrations of sample intracardiac electrograms (IEGMs) showing abnormal cardiac rhythms recognized as precursors to malignant cardiac arrhythmias, including ventricular tachycardia (FIG. 7A), ventricular couplets (FIG. 7B) and premature ventricular complexes (FIG. 7C), detected by an antiarrhythmia pacemaker of the present invention.
Figure 7B:
Figure 7C:
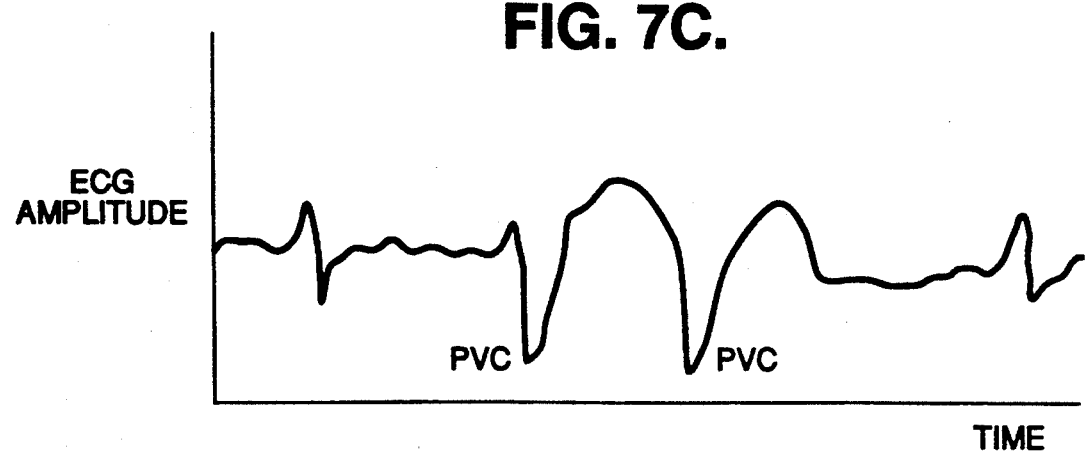
Figure 8A:
FIGS. 8A and 8B are illustrations of samples of the detailed morphology of IEGM forms which are recognized as precursors to malignant cardiac arrhythmias, including premature ventricular depolarizations (FIG. 8A) and repolarization abnormalities such as long QT interval (FIG. 8B), detected by an antiarrhythmia pacemaker of the present invention.
Figure 8B:
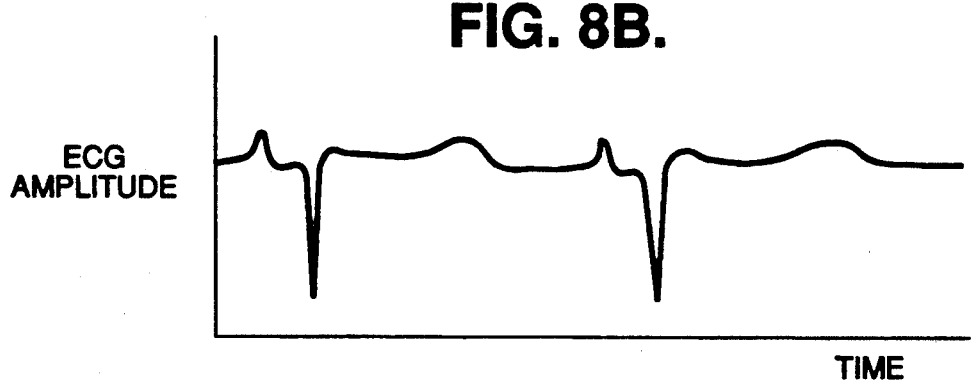

The pacemaker 17 of FIG. 1 acquires intracardiac electrogram (IEGM) samples which the microprocessor 19 monitors and analyzes to detect arrhythmia precursors. Some IEGM features are known to occur in patients experiencing potentially lethal ventricular tachyarrhythmias. Two types of precursors have been identified which are antecedent to ventricular fibrillation or sudden death relating to: (a) abnormal ventricular rhythms, and (b) abnormal electrocardiogram polarization waveforms. FIG. 7A-7C illustrate ventricular fibrillation precursors displaying abnormal ventricular rhythms in the form of complex ventricular arrhythmias, including ventricular tachycardia (FIG. 7A), ventricular couplets (FIG. 7B) and premature ventricular complexes (PVCs in FIG. 7C). The degree of complexity of such ventricular arrhythmias (for example, dynamic oscillations in the rate of emergence of ventricular tachycardia or wild variations in the length of ventricular tachycardia outbursts) and an increasing rate of occurrence of ventricular arrhythmias are as important as the presence of such features in the detection of precursors. Density of ventricular arrhythmias, defined as the ratio of abnormal to normal ventricular rhythms, is also helpful for diagnosing harmful arrhythmias.

Precursors which are characterized primarily by abnormalities in the IEGM waveform, rather than by abnormalities in cardiac rate or rhythm, are shown in FIGS. 8A, 8B and 9A-9C and include: repolarization abnormalities, ST-segment changes and late potentials. The microprocessor 19 must analyze fine detail within the IEGM waveforms to detect waveform abnormality precursors. The microprocessor analyzes the fine detail of IEGMs to detect R-on-T ventricular premature depolarizations (FIG. 8A) which frequently initiate malignant arrhythmias, repolarization abnormalities such as a prolonged QT intervals (FIG. 8B), and ST-segment changes (FIGS. 9A and 9B, ST-segment elevation and depression). All these events have diagnostic significance for predicting imminent ventricular fibrillation. Late potentials (designated LP in FIG. 9C) also anticipate episodes of ventricular tachycardia or fibrillation.

The timing of particular precursors, as well as their presence, is diagnostically important for determining the onset and risk of sudden death. In many cases of sudden cardiac death, the first indications of arrhythmia are a maximum incidence of intermediately frequent (from 100 to 500 per hour) premature ventricular complexes occurring between fifteen and six hours prior to ventricular fibrillation. This is followed by an increased frequency in ventricular couplets and runs of complex ventricular arrhythmias, including ventricular tachycardia. Repolarization abnormalities often appear in the IEGM waveform several hours before ventricular fibrillation. Often there is an increased incidence of ST-segment changes having an amplitude greater than 2 mm throughout the risk period and lasting until the third hour prior to sudden death. Within the three hours prior to sudden death, ST-segment changes of this amplitude diminish in incidence. Over the final six hours preceding sudden death there is an increased incidence of lower amplitude ST-segment changes, usually in the direction of elevation. During these final hours the ST-segment change gradually diminishes from a high amplitude toward the baseline.

Figure 10:
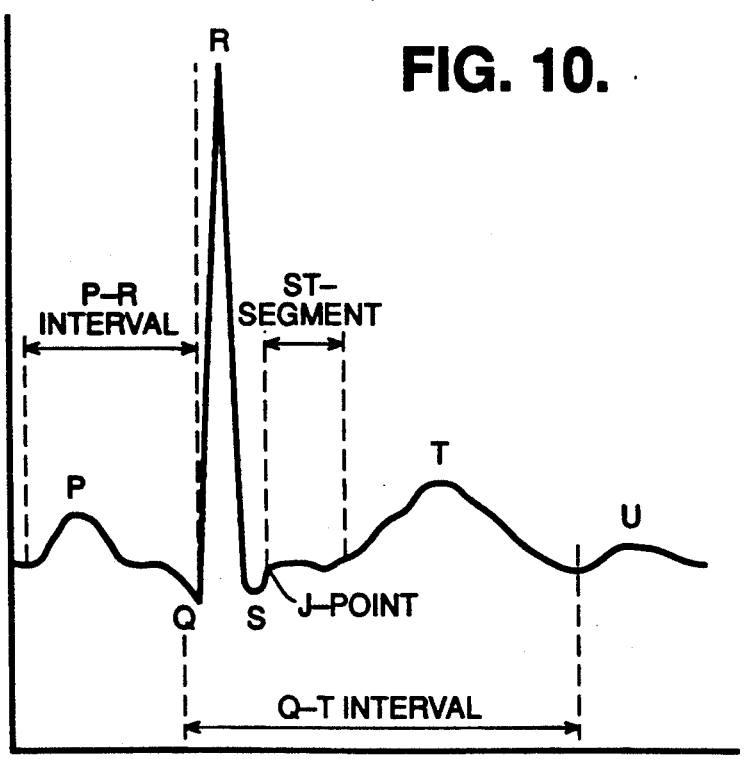
FIG. 10 is an illustration of a normal electrocardiogram signal.

The microprocessor 19 constantly acquires IEGM signals and from these detects ventricular events and analyzes the fine detail of portions of the signal using known analytical techniques. Much of the diagnostic detail of an IEGM lies in the vicinity of the QRS-complex. FIG. 10 illustrates a waveform of a normal cardiac cycle with conventional timing intervals indicated therein. S-T and Q-T intervals end, respectively, at the beginning and end of the T-wave. Normal P waves have a duration ranging from 0.04 to 0.08 seconds and precede the R wave (the P-R interval) by from 0.12 to 0.20 seconds. The QRS-complex, which begins with the Q wave and ends with the S-wave, normally has a duration of 0.04 to 0.10 seconds For each cardiac cycle, the microprocessor 19 performs the operations shown in the flow diagram of FIG. 11. Generally, the microprocessor identifies cardiac events, correlates the events with time intervals within the cardiac cycle, and analyzes the detailed structure within the IEGM. While sensing IEGM signals, the microprocessor first searches for the R wave within the present cardiac cycle in block 303. The R wave normally has the largest slope within the cardiac cycle (the greatest change in polarization amplitude in a short time) and a large amplitude. The preferred embodiment of the invention uses a delta comparator, a slope detector, to detect the R wave. The microprocessor continuously samples in block 300 until it detects an R wave in block 303. As part of the sampling process in block 300, the microprocessor saves data relating to morphology of the QRS-complex for further analysis This data may include samples of IEGM amplitude, maximum positive and negative polarity excursions and derivatives (slopes) of the leading and trailing edge of the QRS-complex. After detecting the R wave the microprocessor determines the elapsed time since the last R wave in block 305. The reciprocal of the elapsed time is the instantaneous heart rate for the present cycle. The microprocessor calculates this reciprocal value and averages the instantaneous rate over a few cardiac cycles (for example, four) to determine the average rate in block 310. In block 313, the microprocessor compares the current average rate to predetermined limit values. These limits reflect the rates of various types of arrhythmias. The limits may vary, depending on certain physiological characteristics, indicative of exercise, for example. Standard rate-responsive sensors may be used for this purpose. Therefore, before the test in block 313, the rate limits are set in block 311 in accordance with whichever standard rate-response parameter is monitored.

If the average rate lies within the boundaries set for a particular class of ventricular arrhythmia in block 313, the microprocessor (in block 315) tests the morphology of details within the QRS-complex against predetermined and stored morphology parameters to classify the rhythm as either an arrhythmia or a normal rhythm. If the microprocessor detects an arrhythmia, it classifies the arrhythmia according to type and logs the occurrence of the particular arrhythmia type in memory in block 317.

In block 320 the microprocessor processes subsequent samples and analyzes the IEGM signal from the R wave to the T wave to determine the QT interval and to diagnose myocardial ischemia from ST-segment morphology. The ST-segment occurs in the sampling window beginning at the J-point following a QRS-complex, as is known in the art (see FIG. 10), and persists for at least 80 milliseconds. ST-segment depression, defined (according to programming of the microprocessor) as a horizontal or downsloping shift of 0.1 mV (some researchers use 0.2 mV or 0.3 mV) during the ST-segment which endures for at least 30 seconds in consecutive heartbeats (some researchers use from 40 to 60 seconds), correlates positively with myocardial ischemia both in exercise tolerance tests and in ambulatory testing of resting patients and patients performing daily activities. Most patients with stable angina and proven coronary artery disease frequently have episodes of ST-segment depression during daily life. ST-segment changes warn of injury to myocardial tissue, even in patients afflicted with otherwise asymptomatic silent myocardial ischemia, since they are frequently accompanied by regional disturbances of myocardial perfusion and disturbances of left ventricular function. The microprocessor analyzes the waveform to determine when the T wave occurs (it should arrive within 400 milliseconds of the R wave) within the current cardiac cycle. After detecting the R wave, the microprocessor may change the acquisition parameters of the IEGM signal (for example, by selecting a different set of impedances in an input amplifier to adjust the bandwidth) to better analyze the waveform structure following the R wave.

Referring back to FIG. 10, immediately after the comparator detects an R wave, the microprocessor 19 processes the IEGM to measure the leading and trailing R wave slopes, then continues to track the signal down the S wave and back up until the slope diminishes at what is called the J-point. While processing the IEGM (in block 320 of FIG. 11) from the J-point until the waveform crosses the baseline (tested in block 323), the microprocessor integrates and determines the slope of the signal. If the magnitude (the absolute value) of the integrated signal is larger than at least one predetermined value and remains larger for a consecutive number of cardiac cycles lasting a predetermined time (for example, 40 seconds), then the microprocessor classifies this event as an ST-segment elevation. If the integrated signal is below the baseline (a negative signal) and the slope is level or negative, then the microprocessor classifies the event as ST-segment depression, an indication of ischemia. If the ST-segment is either elevated or depressed by a value greater than a predetermined value (block 325 of FIG. 11) the microprocessor stores a code in memory to identify this incidence in block 327. If the ST-segment is abnormal, either depressed or elevated, the microprocessor may use the total duration of deviation persistence as an index of ischemia.

Figure 9A:
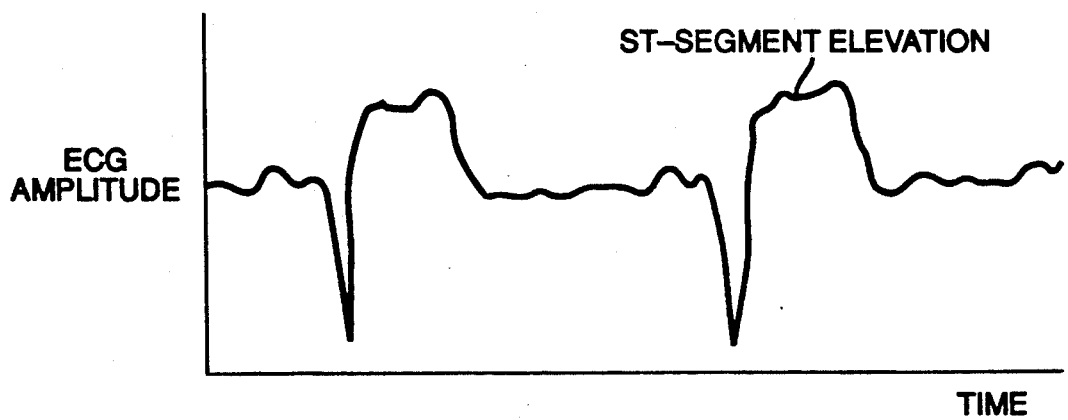
FIGS. 9A-9C are additional illustrations of samples of the detailed morphology of IEGMs which are recognized as precursors to malignant cardiac arrhythmias, including ST-segment elevation (FIG. 9A), ST-segment depression (FIG. 9B) and late potentials (FIG. 9C), detected by an antiarrhythmia pacemaker of the present invention.
Figure 9B:
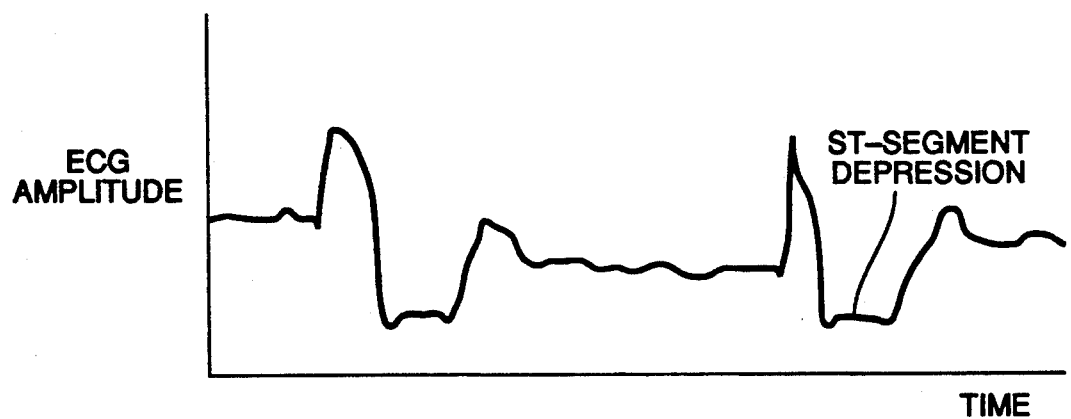
Figure 9C:
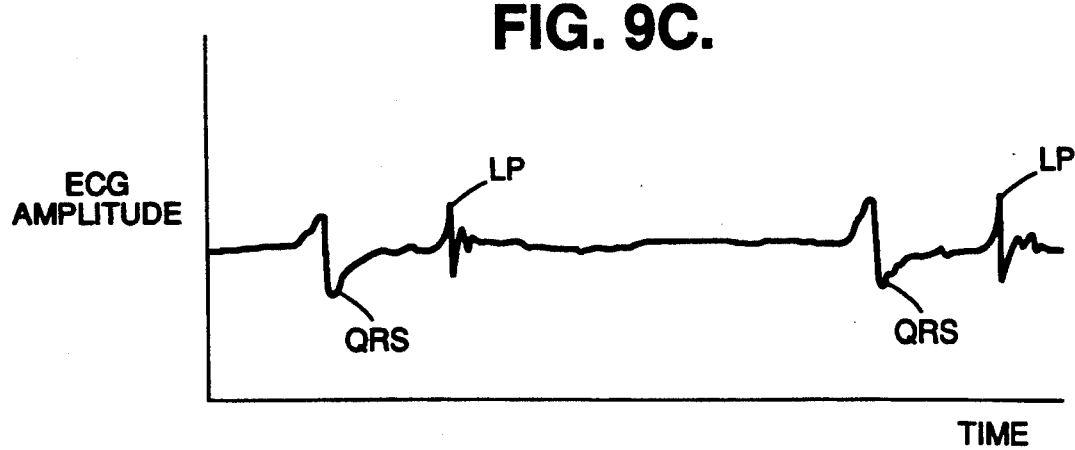

Also in block 320, while processing the IEGM following the QRS-complex, the microprocessor 19 analyzes the data to determine the presence, amplitude, frequency content and duration of late potentials (FIG. 9C). The presence of late potentials predicts subsequent episodes of ventricular tachycardia, possibly leading to ventricular fibrillation and sudden cardiac death. Late potentials are fluctuations in IEGM signal amplitudes occurring more than 10 milliseconds after the QRS-complex. The amplitude, frequency content and duration of the late potential are diagnostically significant for predicting the occurrence of ventricular tachycardia and ventricular fibrillation. In an operation distinct from the ST-segment processing, the microprocessor analyzes the samples beginning about 10 milliseconds following the end of the QRS-complex and persisting for up to 125 milliseconds. In the preferred embodiment of the invention this analysis may include: (1) determining the peak positive and negative deflections of the signal from the baseline amplitude, (2) detecting the presence and duration of the late potential by detecting the first (if any) and last samples wherein the deflection from baseline is greater than a predetermined amplitude within the late potential window, (3) averaging the late potential signal for the present cardiac cycle with that of previous cycles beginning with the first sample having an amplitude greater than the predetermined trigger amplitude, and (4) performing Fourier analysis of the data within the late potential sample window. If the late potential is present and has an amplitude greater than a predetermined level, the microprocessor logs a code signifying the presence of the late potential as well as the amplitude, duration and one or more parameters specifying frequency content information in block 327 of FIG. 11.

In block 330 the microprocessor 19 continues to process the IEGM to detect the end of the T wave or the occurrence of an R wave (block 333). If the next R wave occurs during the T wave (block 335), the microprocessor notes this abnormality and stores a code in memory reflecting the incidence of an R-on-T beat in block 337. At the end of the T-wave in block 340 the microprocessor determines the QT-interval illustrated in FIG. 10. In block 340, the microprocessor normalizes the QT-interval to cardiac cycle time (R-R) in accordance with standard techniques. In block 343, the microprocessor compares the normalized QT-interval with a predetermined threshold QT-interval value to detect abnormalities in repolarization (see FIG. 8B). If an abnormality occurs the microprocessor stores a code to signify the event in block 345.

The microprocessor 19 may designate a separate circular buffer for each of the precursor events (ventricular arrhythmia, a particular type of ventricular arrhythmia, ST-segment changes, and repolarization) or it may tag each type of precursor with an identifying code and store it in a single circular buffer. Upon the identification of any of the precursors (block 350), the microprocessor will also update a similar circular buffer memory (block 353) to store the rate of precursor occurrences of any type. If, upon updating the precursor rate buffer, the microprocessor detects a rate greater than a predetermined value or otherwise flags a dangerous situation (block 355), the microprocessor will update a warning memory and may initiate a precursor therapy in block 357, as will be described hereinafter.

The technique for modifying autonomic nervous system activity is based on an understanding of the mechanism by which nervous tone influences the formation of arrhythmias. According to P. J. Schwartz et al. in "The Rational Basis and the Clinical Value of Cardiac Sympathetic Denervation in the Prevention of Malignant Arrhythmias", *European Heart Journal*, Vol. 7, Supp A, pages 107–118 (May 86), left cardiac sympathetic stimulation delivered to the left stellate ganglion (LSG) induces ventricular tachyarrhythmias by causing asymmetry in the sympathetic outflow to the heart which increases the dispersion of ventricular refractory periods. This occurs because adrenergic stimulation, mediated by the action of catecholamines, is associated with action potential and refractory period shortening which increases the electrical inhomogeneity of the myocardium. Thus re-entrant conduction circuits in the heart arise, leading to an arrhythmia episode. Vagal activation can modify the occurrence of arrhythmias to prevent ventricular fibrillation. Vagal stimulation blunts the effect of catecholamines by acting at either a presynaptic or postsynaptic level on the sympathetic nerve transmission to potentially counteract the effect of catecholamines on automaticity and refractory period.

M. Stramba-Badiale et al., in "Sympathetic-parasympathetic Interaction and Accentuated Antagonism in Conscious Dogs", *American Journal of Physiology*, V260 (2Pt 2): H335340 (Feb. 1991) found that the heart response to vagal stimulation is enhanced in the presence of elevated sympathetic activity. Therefore, when the microprocessor detects the occurrence of an arrhythmia, either tachycardia or fibrillation, this is evidence of elevated sympathetic activity. Thus, in addition to performing an antiarrhythmia pacing therapy, the microprocessor, in the arrhythmia therapy block 143 of FIG. 6, directs the generation of stimulation pulses to parasympathetic nerves or ganglia to suppress the sympathetic influence on heart rate. These stimulation pulses are in the form of repetitive, brief bursts of pulses, rather than single, equally spaced pulses. These pulses are delivered in a manner which is analogous to natural vagal activity. Increasing vagal stimuli frequency causes an overall lengthening of P—P interval and a decrease in arrhythmia rate. The applied current may have a stimulation intensity ranging from 1 to 3 mA.

In one method of stimulation, ten trains of vagal pulses may be delivered at progressively increasing frequencies of stimulation, such as 2, 4, 6, 8, 10, 12 Hz in 1-min intervals. One example of this method of nerve stimulation is illustrated in FIGS. 12A through 12D, which depicts surface electrocardiograms (ECGs) of ventricular tachycardia waveforms, an antitachycardia pacing stimulus (ATP) applied to the heart, and nerve stimulations (NS) delivered at different rates. The antitachycardia pacing stimulus applied to the heart is preferably of the type disclosed in U.S. Pat. No. 4,390,021 to R. A. J. Spurrell et al., issued Jun. 28, 1983, entitled "Two Pulse Tachycardia Control Pacer". This patent discloses a pacemaker for controlling tachycardia in which the coupled interval, as well as the initial delay, is scanned. The time parameters which are successful in terminating the tachycardia are stored so that upon confirmation of another tachycardia event, the previously successful time parameters are the first ones to be tried. The device also allows tachycardia to be induced by the physician to allow for programming of the initial delay and the coupled interval parameters.

Figure 12A:
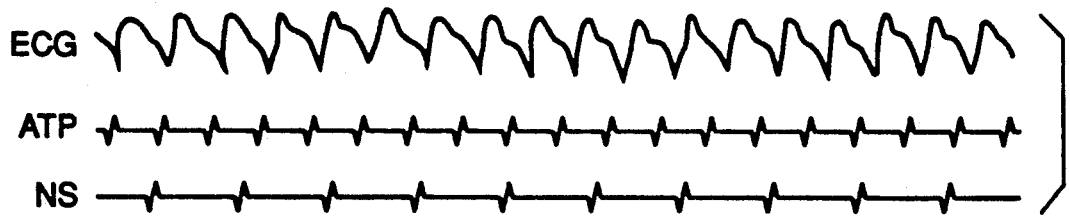
FIGS. 12A-12D depict surface electrocardiograms (ECGs) of ventricular tachycardia waveforms, with a constant antitachycardia pacing stimulus (ATP) applied to the heart, and with progressively increasing rates of nerve stimulation (NS)
Figure 12B:
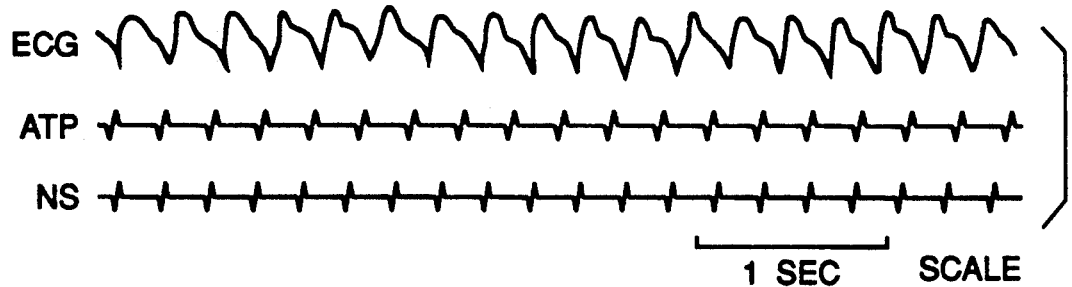
Figure 12C:
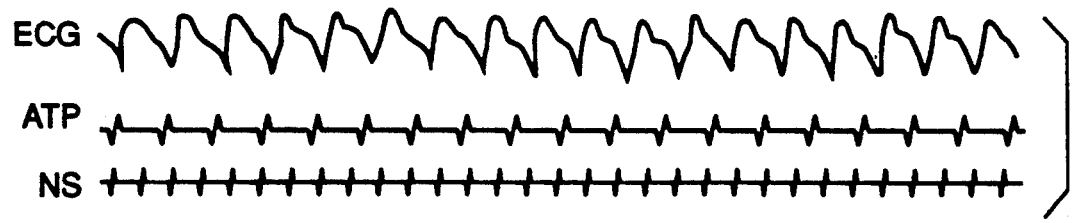
Figure 12D:
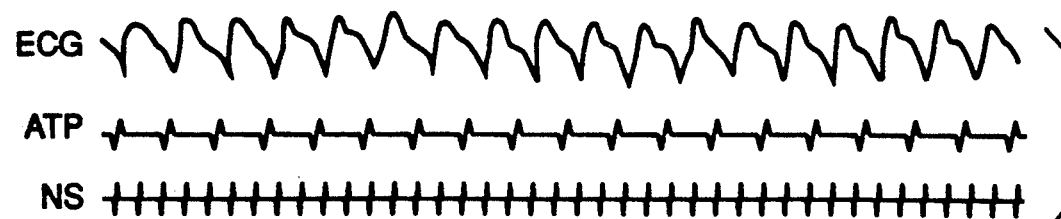

FIG. 12A depicts nerve stimulation (NS) delivered at 2 Hz. FIGS. 12B through 12D illustrate nerve stimulation delivered at 4 Hz, 6 Hz and 8 Hz, respectively. In this method of stimulation, each train of pulses may be sustained for 10 sec with a pulse duration of 3 to 5 ms. An appropriate intensity of stimulation may be determined for the pulse delivery rate selected by increasing the current delivered by each pulse until the heart rate slows to a desired, stable level.

Another example of an antitachycardia pacing technique which may be used to augment neural stimulation to correct a cardiac arrhythmia is U.S. Pat. No. 3,942,534 to Spurrell et al. This patent discloses a pacer which, following detection of a tachycardia, generates an atrial (or ventricular) stimulus after a delay interval. If that stimulus is not successful in terminating the condition, then another stimulus is generated after another premature heartbeat following a slightly different delay. The device constantly adjusts the delay interval by scanning through a predetermined delay range. Stimulation ceases as soon as the heart is restored to sinus rhythm. If successful reversion is not achieved during one complete scan, then the cycle is repeated. The device further provides a second stimulus following the first, both stimuli occurring within the tachycardia cycle, i.e. before the next naturally occurring rapid beat. The time period between a heartbeat and the first stimulus is known as the initial delay, while the time period between the first stimulus and the second stimulus is known as the coupled interval. In this device, once the coupled interval is set by a physician it is fixed, and therefore the second stimulus always occurs a predetermined time after the first stimulus, no matter when the first stimulus occurs after the last heartbeat or how fast is the rate of the tachycardia. Additional examples of antitachycardia pacing techniques which may be used to augment neural stimulation are listed below.

U.S. Pat. No. 4,398,536 of Nappholz et al., entitled "Scanning Burst Tachycardia Control Pacer", issued Aug. 16, 1983, discloses a scanning burst tachycardia control pacer. Following each tachycardia confirmation, a burst of a programmed number of stimulating atrial (or ventricular) pulses is generated. The rates of the bursts increase from cycle to cycle whereby following each tachycardia confirmation, a pulse burst at a different rate is generated. The rate of a burst which is successful in terminating tachycardia is stored, and following the next tachycardia confirmation, the stored rate is used for the first burst which is generated.

In U.S. Pat. No. 4,406,287 invented by T. A. Nappholz et al., issued Sep. 27, 1983, entitled "Variable Length Scanning Burst Tachycardia Control Pacer", there is disclosed a variable length scanning burst tachycardia control pacer. The physician programs the maximum number of pulses in a burst. The number of pulses in a burst is scanned, and the number which is successful in terminating tachycardia is registered so that it is available for first use when a new tachycardia episode is confirmed. Successive bursts, all at the same rate, have different numbers of pulses, the pulse number scanning being in the upward direction. If all bursts are unsuccessful, a new rate is tried and the number scanning begins over again. Thus all combinations of rates and pulse numbers are tried, with the successful combination being used first following the next tachycardia confirmation.

U.S. Pat. No. 4,408,606 to R. A. J. Spurrell et al., entitled "Rate Related Tachycardia Control Pacer", issued Oct. 11, 1983, discloses a rate related tachycardia control pacer. Following tachycardia confirmation, a burst of at least three stimulating pulses is generated. The time intervals between successive pulses decrease by a fixed decrement; hence the rate of the pulses increases during each cycle of operation. The first pulse is generated following the last heartbeat which is used to confirm tachycardia at a time which is dependent on the antitachycardia rate. The time delay between the last heartbeat and the first pulse in the burst is equal to the time interval between the last two heartbeats less the fixed decrement which characterizes successive time intervals between stimulating pulses.

Figure 11:
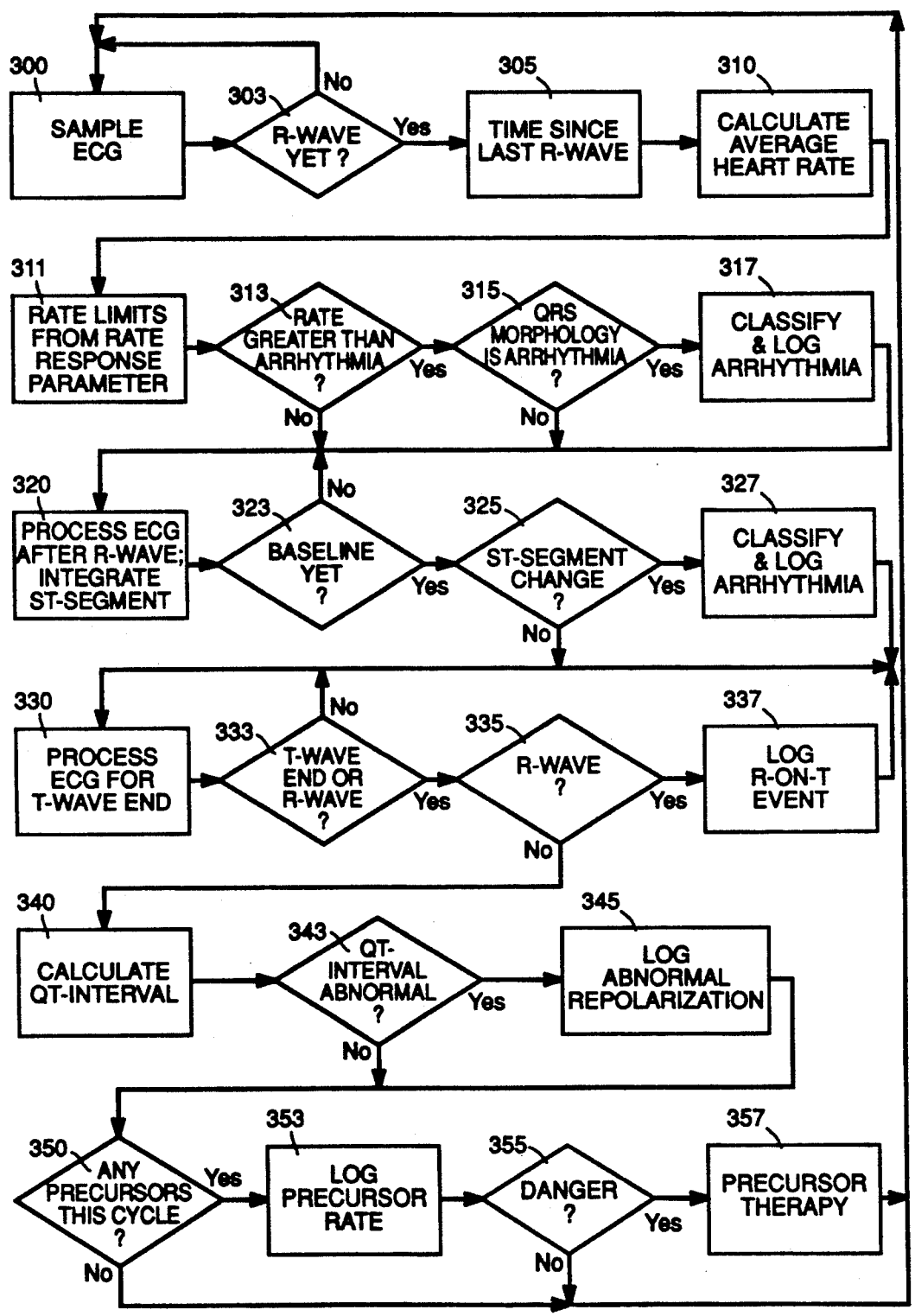
FIG. 11 is a flow diagram illustrating the method performed by an antiarrhythmia pacemaker of the present invention for detecting precursors of malignant cardiac arrhythmias.
Figure 13A:
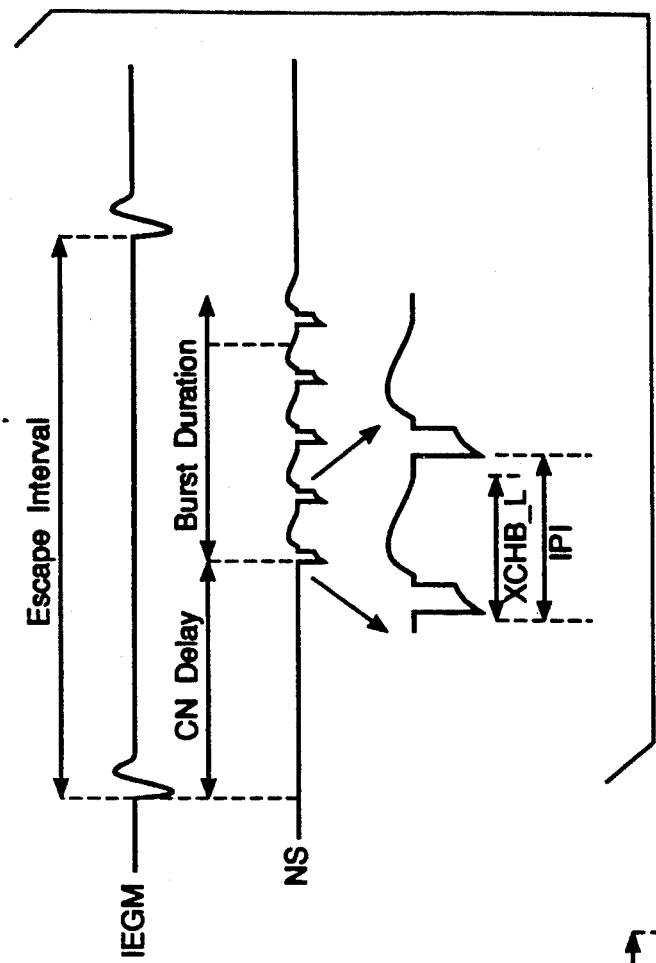
Figure 13B:
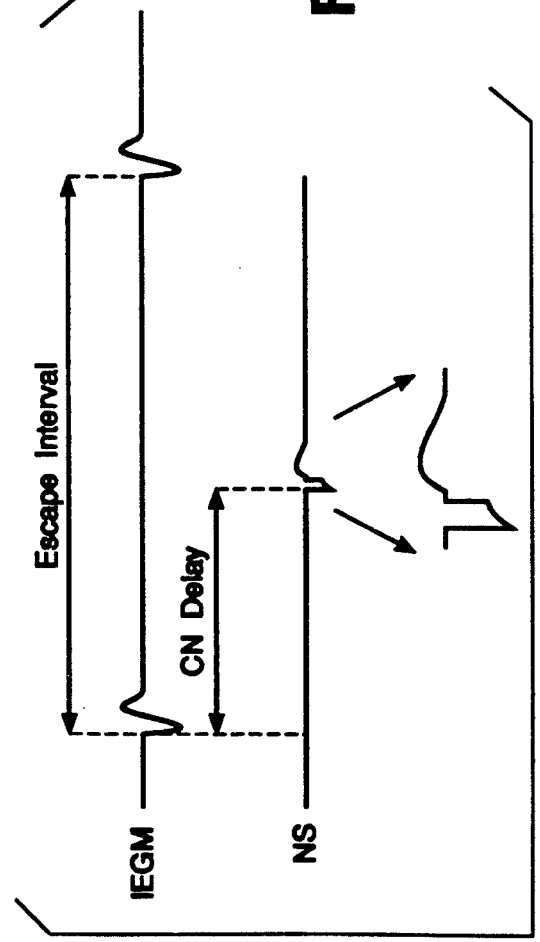

Even in the absence of an arrhythmia condition, the antiarrhythmia pacemaker of the present invention monitors cardiac activity to detect arrhythmia precursors, such as episodes of myocardial ischemia. When acute myocardial ischemia occurs, vagal activation tends to prevent fibrillation in a manner that is partly dependent on direct electrophysiological effects and largely secondary to the decrease in heart rate which results in the reduced oxygen consumption associated with ischemia. This protective effect of vagal stimulation follows from its ability to decrease heart rate. Therefore, upon detection of an arrhythmia precursor, the microprocessor 19 in precursor therapy block 357 of FIG. 11 directs a therapy which prevents ventricular fibrillation by vagal stimulation during acute myocardial ischemia. In the preferred embodiment of the invention, the technique of vagal stimulation employed in response to detection of an arrhythmia precursor in precursor therapy block 357 of FIG. 11 is different from the technique utilized in response to detection of an arrhythmia. Referring to FIG. 13A and FIG. 13B, in response to the detection of a precursor, the microprocessor controls vagal stimulation to provide brief vagal stimulation in which a single stimulus (FIG. 13B) or brief burst of stimuli (FIG. 13A) act to reduce heart rate temporarily. This influence on heart rate depends on the timing within the cardiac cycle at which the vagal stimulation is delivered. M. N. Levy et al., in "Parasympathetic Control of the Heart", Nervous Control of Vascular Function, Randall WC ed., Oxford University Press (1984), found that stimulation of the vagus nerve at the time of detecting a P-wave caused a P—P interval increase of about 80% as compared to the P—P interval for no vagal stimulation. Delaying vagal stimulation from the time of P-wave detection caused further increases in P—P interval such that increasing delays resulted in larger intervals to a maximum increase in P—P interval of about 95%, which occurred with a post P-wave delay of about 225 ms. Further increases in delay duration prior to delivery of vagal stimulation caused a progressive diminution of P—P interval until the P—P interval reached a minimum length equal to the P—P interval without vagal stimulation.

In contrast to Levy's work, one embodiment of the present invention employs electrical stimulation of both cardiac and autonomic nervous system tissue. FIG. 13A and FIG. 13B illustrate a comparison of cardiac stimulation and neural stimulation timing as controlled by the antiarrhythmia pacemaker of the present invention. Cardiac cycle timing is shown in an intracardiac electrogram (IEGM) trace. Neural stimulation (NS) is shown relative to the IEGM. In this it is assumed that the pacemaker has previously detected an arrhythmia precursor but not a confirmed arrhythmia cardiac rate.

The pacemaker has previously measured the natural current cardiac rate and has established a corresponding interval. To perform overdrive pacing, the pacemaker decreases the natural interval by a predetermined amount or predetermined percentage and begins generating cardiac pacing pulse stimulations at the new rate. The new interval between paces is labelled "Escape Interval" in FIG. 13A and FIG. 13B. The antiarrhythmia pacemaker waits a predetermined cardio-neural delay (CN Delay) amount, then begins stimulating the vagal cervical ganglion. If the pacemaker is programmed to generate multiple pulses within a burst, as shown in FIG. 13A, the predetermined parameters of Burst Duration and interpulse interval (IPI) determine the form of the burst. Multiple pulse bursts are preferred in the case of confirmed arrhythmias. The pacemaker does not sense cardiac signals during the cross-channel blanking interval (XCHB_L) to prevent sensing of noise and confusion of noise with an intrinsic cardiac signal. Note that a vagal stimulation in the form of a single pulse or a short burst of pulses may not be an appropriate therapy in response to the detection of a high rate arrhythmia because repetitive stimulation of parasympathetic nerves, at a rate similar to the heart rate, tends to entrain S-A nodal pacemaker cells, so that the heart rate will take on the same frequency as that of vagal stimulation. Therefore, for high rate arrhythmias, single pulse or short burst neural stimulation could lead to heart rates which are inappropriately high during pacing.

Various embodiments of the invention detect particular combinations of abnormal cardiac rhythms and respond with cardiac antiarrhythmia and nerve stimulation therapy. Such abnormal rhythms may occur with respect to either the atrial chamber, the ventricular chamber or both chambers of the heart. One particularly important embodiment of the present invention detects atrial fibrillation and responds to such detection by performing a cardiac pacing stimulation therapy within the atrial chamber, the ventricular chamber or both chambers of the heart, in combination with nerve stimulation which slows the atrial rate. Preferably, this nerve stimulation is in the form of repetitive brief bursts of electrical energy. This embodiment of the invention is important because delivery of a cardiac pacing therapy in response to detection of atrial fibrillation, without performing nerve stimulation, tends to aggravate the atrial fibrillation condition, possibly leading to the generation of a ventricular fibrillation condition, a much more dangerous phenomenon.

Figure 15:
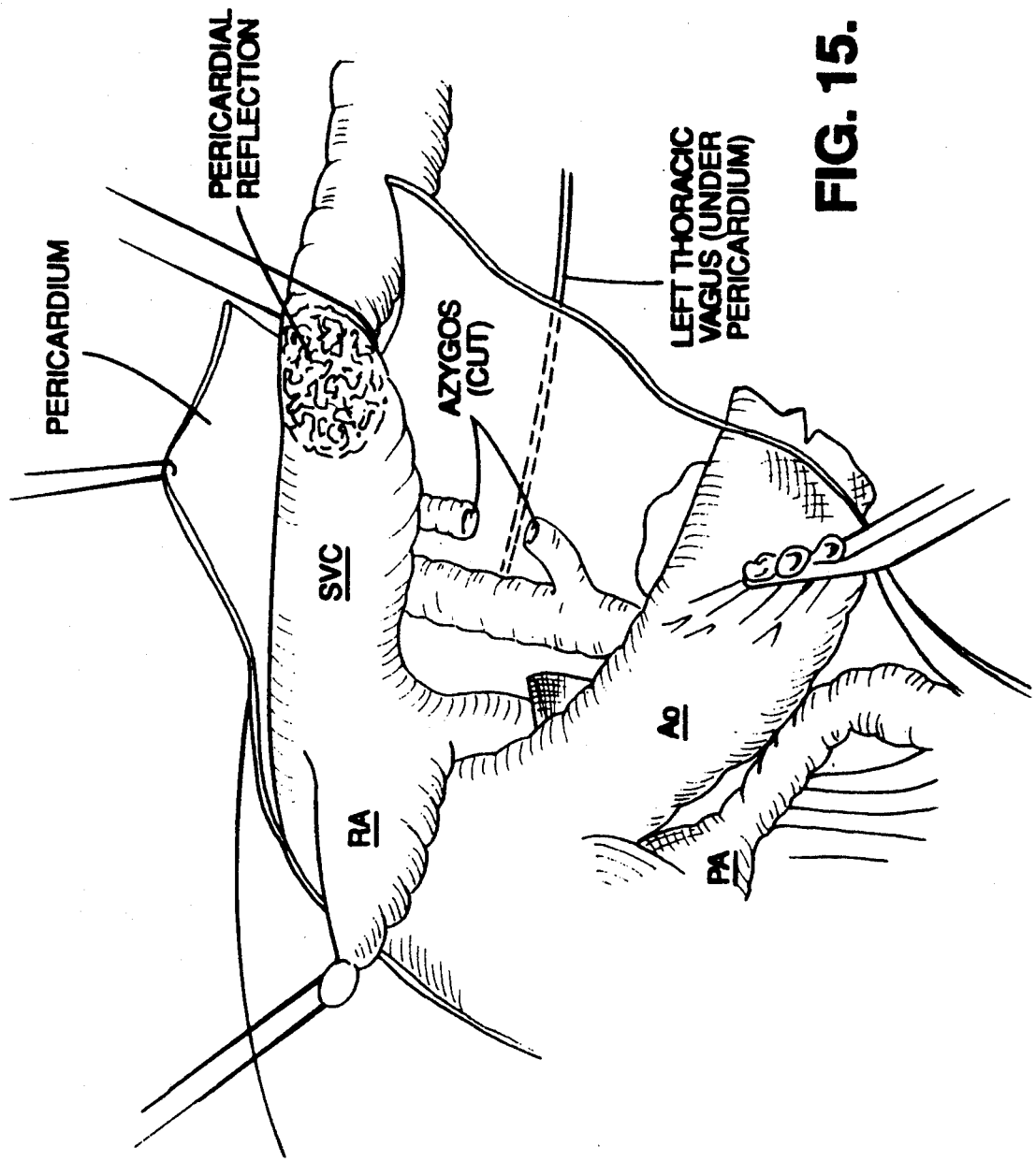
FIG. 15 depicts a right lateral view of the heart, showing the relationship of the vagus nerve in relation to the major blood vessels on the right side of the heart.
Figure 16:
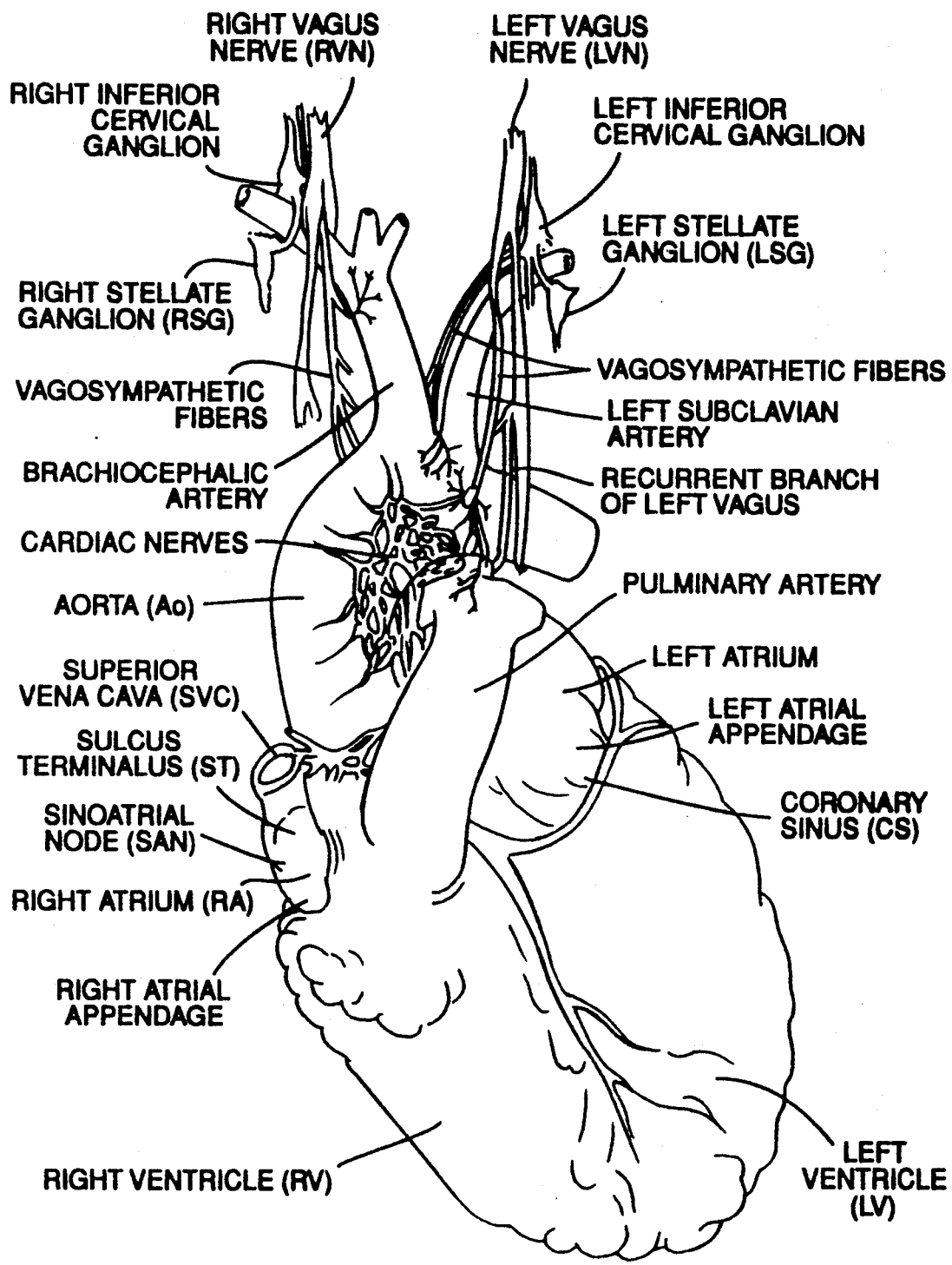
FIG. 16 illustrates a diagrammatic representation of an anterior view of a dog's heart, particularly characterizing the anatomical relationship of autonomic nervous system components with respect to cardiovascular system structures.

FIG. 14, 15 and 16, taken in combination, illustrate the anatomy of cardiovascular and neural structures in a dog. FIG. 14 depicts a left lateral view of the heart illustrating sympathetic and parasympathetic autonomic innervation of the A-V nodal region of a canine heart. FIG. 15 depicts a right lateral view of the heart, showing the anatomical relationship of the left thoracic vagus nerve with respect to the major blood vessels on the right side of the heart. FIG. 16 illustrates a representation of an anterior view of a dog's heart including a depiction of important blood vessels and autonomic nervous system elements.

Most parasympathetic and sympathetic pathways, which are referenced generally by the term "Vagosympathetic Fibers" in FIG. 16, innervate the sino-atrial node (SAN) in FIG. 16 via nerves which enter the heart along the superior vena cava (SVC), shown in FIGS. 14, 15 and 16. Other parasympathetic nerve fibers enter the heart between the right (not shown) and left superior pulmonary veins (LSPV in FIG. 14). Still other parasympathetic fibers enter the heart over the superior right atrium (not shown) and over the junction between the inferior vena cava (IVC of FIG. 14) and the inferior atria (not shown). FIG. 14 illustrates the distribution of primary cardiac nerves on the left side of the heart and sympathetic innervation of the AV node (AVN). One autonomic pathway, which is made up of branches of the ventromedial cervical cardiac nerve (VMCCN) and the ventrolateral cervical cardiac nerve (VLCCN), passes along the pulmonary artery (PA) to the A-V junctional region (AVJ). Other nerves, including branches of the VLCCN and the innominate nerve, penetrate the pericardium and pass over the pulmonary artery (PA) and pulmonary veins (PV) to enter the heart at the junction of the inferior vena cava (IVC) and the inferior left atrium (ILA). The ventrolateral cervical cardiac nerve (VLCCN) contains major sympathetic inotropic fibers. Activity of these nerves influences the force or energy of muscle contractions. Sympathetic chronotropic fibers, which regulate the timing of cardiac muscle contractions, approach the heart either in peripulmonary tissues (not shown) or along the superior vena cava (SVC) and pulmonary veins, for example, the left superior, medial and inferior pulmonary veins (LIPV, LMPV and LSPV). Parasympathetic fibers enter the heart along and between the right (not shown) and left superior pulmonary veins (LSPV), around the coronary sinus (CS in FIG. 16), and along the superior vena cava (SVC).

The preferred embodiment of the antiarrhythmia pacemaker invention employs direct electrical stimulation of parasympathetic fibers within either the left or the right stellate ganglion (see FIGS. 14 and 16) to increase vagal tone, reduce heart rate, elevate fibrillation threshold and decrease defibrillation threshold. Other embodiments of the invention may involve stimulation of a stellate ganglion or a caudal cervical ganglion (not shown) to elicit various changes in dromotropic, chronotropic and inotropic aspects of the heart's overall performance.

Stimulation of more distal branches of these structures, such as the left thoracic vagus nerve, may provide more precise control of heart function. For example, Levy et al. found two locations on the epicardium of the heart for which electrical stimulation will trigger nerves en route to the sino-atrial node (SAN of FIG. 16) and the atrio-ventricular node (AV node of FIG. 14). Referring to FIG. 16, the intercaval region of the right atrium (RA), just posterior to the sulcus terminalis (ST) at the anterior, superior border of the heart's triangular fat pad (not shown) defines a sinoatrial node stimulation area. Selective stimulation of cardiac intracardiac nerves at this site produces slowing in the sinus rate without a change in intra-atrial conduction, A-V conduction or refractory period of the atrial muscle. Furthermore, an atrioventricular node stimulation area is located in a pocket between the terminations of the inferior vena cava (IVC of FIG. 14) and the coronary sinus (CS of FIG. 16) at the inferior and posterior portion of the right atrium (RA in FIGS. 15 and 16).

FIG. 15 depicts a right lateral view of the heart, showing the relationship of the left thoracic vagus nerve in relation to the major blood vessels on the right side of the heart. The aorta (Ao) is shown retracted downwardly, as viewed in FIG. 15, to illustrate the superior vena cava (SVC) and the right pulmonary artery (RPA).

From the foregoing discussion, it is apparent that the present invention provides an antiarrhythmia pacemaker which detects and confirms a wide range of abnormal cardiac states including the detection and confirmation of arrhythmia precursor states and, in response to such detection and confirmation, accomplishes substantial improvement in preventing and terminating dangerous cardiac arrhythmias by stimulating parasympathetic nerve fibers to lower heart rate while performing antiarrhythmia electrical stimulation therapy.

Although the invention has been shown and described with reference to particular embodiments, it is to be understood that these embodiments are merely illustrative of the application of the principles of the invention. Numerous modifications may be made therein and other arrangements may be devised without departing from the true spirit and scope of the invention.

I claim:

1. An antiarrhythmia pacemaker for detecting and treating arrhythmia episodes in a patient's heart, comprising:
    means for detecting an occurrence of an abnormal condition of the heart,
    heart stimulating means for generating and delivering, electrical stimulation to the heart,
    at least one nerve stimulation electrode adapted to be placed in electrical contact with preselected nerve fibers within the patient's nervous system,
    nerve fiber pulse stimulating means electrically coupled to said nerve stimulation electrode for generating and delivering stimulating pulses to the preselected nerve fibers, and
    arrhythmia therapy control means responsive to said detecting means for controlling said heart stimulating means and said nerve fiber pulse stimulating means to direct performance of a combined heart and nerve stimulation therapy.

2. An antiarrhythmia pacemaker according to claim 1, wherein said detecting means detects tachycardia and fibrillation episodes and wherein said arrhythmia therapy control means selects and directs an appropriate parasympathetic autonomic nervous system stimulation therapy in the form of repetitive brief bursts of electrical pulses in combination with an appropriate heart therapy selected from the group of antitachycardia pacing, cardioversion and defibrillation.

3. An antiarrhythmia pacemaker according to claim 2, wherein said parasympathetic autonomic nervous system stimulation therapy is delivered in synchrony with the patient's cardiac cycle.

4. An antiarrhythmia pacemaker according to claim 2, wherein said parasympathetic autonomic nervous system stimulation therapy is electrical stimulation of the patient's vagal cervical ganglion.

5. An antiarrhythmia pacemaker according to claim 1, wherein said detecting means detects precursors to malignant cardiac arrhythmias and wherein said arrhythmia therapy control means selects and directs an appropriate parasympathetic autonomic nervous system stimulation therapy in the form of single electrical pulses in combination with an appropriate heart pacing therapy selected from the group of bradycardia pacing support, overdrive pacing and antitachycardia pacing.

6. An antiarrhythmia pacemaker according to claim 5, wherein said parasympathetic autonomic nervous system stimulation therapy is delivered in synchrony with the patient's cardiac cycle.

7. An antiarrhythmia pacemaker according to claim 5, wherein said parasympathetic autonomic nervous system stimulation therapy is electrical stimulation of the patient's vagal cervical ganglion.

8. An antiarrhythmia pacemaker according to claim 5, wherein said detecting means detects precursors to malignant cardiac arrhythmias, said precursors being selected from the group including ventricular tachycardia, ventricular couplets, premature ventricular complexes, premature ventricular depolarizations, repolarization abnormalities, ST-segment elevation, ST-segment depression and late potentials.

9. An antiarrhythmia pacemaker according to claim 1, wherein said detecting means detects precursors to malignant cardiac arrhythmias and episodes of tachycardia and fibrillation and wherein said arrhythmia therapy control means selects and directs an appropriate parasympathetic autonomic nervous system stimulation therapy in the form of electrical pulses in combination with an appropriate heart therapy selected from the group of bradycardia pacing support, overdrive pacing, antitachycardia pacing, cardioversion and defibrillation.

10. An antiarrhythmia pacemaker according to claim 9, wherein said parasympathetic autonomic nervous system stimulation therapy is delivered in synchrony with the patient's cardiac cycle.

11. An antiarrhythmia pacemaker according to claim 9, wherein said parasympathetic autonomic nervous system stimulation therapy is electrical stimulation of the patient's vagal cervical ganglion.

12. An antiarrhythmia pacemaker according to claim 9, wherein said detecting means detects precursors to malignant cardiac arrhythmias, said precursors being selected from the plets, premature ventricular complexes, premature ventricular depolarizations, repolarization abnormalities, ST-segment elevation, ST-segment depression and late potentials.

13. An implantable atrial defibrillator, comprising:
means for detecting an occurrence of atrial fibrillation,
heart pulse stimulating means for generating and delivering defibrillation stimulating pulses to the heart,
at least one nerve stimulation electrode adapted to be placed in electrical contact with preselected nerve fibers within the patient's nervous system,
nerve fiber pulse stimulating means electrically coupled to said nerve stimulation electrode for generating and delivering stimulating pulses to the preselected nerve fibers, and
defibrillation therapy control means responsive to said detecting means for controlling said heart pulse stimulating means and said nerve fiber pulse stimulating means to direct performance of a combined heart and nerve stimulation therapy.

14. An implantable atrial defibrillator according to claim 13, wherein said defibrillation therapy control means selects and directs an appropriate parasympathetic autonomic nervous system stimulation therapy in the form of repetitive brief bursts of electrical pulses delivered prior to generating atrial defibrillation therapy.

15. An implantable atrial defibrillator according to claim 14, wherein said parasympathetic autonomic nervous system stimulation therapy is electrical stimulation of the patient's vagal cervical ganglion.

16. A method for operating an antiarrhythmia pacemaker for detecting and treating arrhythmia episodes in a patient's heart, comprising the steps of:
detecting an occurrence of an abnormal condition of the heart,
generating and delivering stimulating pulses to the heart,
generating and delivering stimulating pulses to at least one nerve stimulation electrode which is placed in electrical contact with preselected nerve fibers within the patient's autonomic nervous system, and
controlling said heart pulse stimulation and said nerve fiber pulse stimulation to direct performance of a combined heart and nerve stimulation therapy in response to said abnormal condition.

17. A method according to claim 16, wherein said detection step detects tachycardia and fibrillation episodes and wherein said controlling step selects and directs an appropriate parasympathetic autonomic nervous system stimulation therapy in the form of repetitive brief bursts of electrical pulses in combination with an appropriate heart stimulation therapy selected from the group of antitachycardia pacing, cardioversion and defibrillation.

18. A method according to claim 17, wherein said parasympathetic autonomic nervous system stimulation therapy is delivered in synchrony with the patient's cardiac cycle.

19. A method according to claim 18, wherein said parasympathetic autonomic nervous system stimulation therapy is electrical stimulation of the patient's vagal cervical ganglion.

20. A method according to claim 16, wherein said detecting step detects precursors to malignant cardiac arrhythmias and wherein said controlling therapy control step selects and directs an appropriate parasympathetic autonomic nervous system stimulation therapy in the form of single electrical pulses in combination with an appropriate heart pacing therapy selected from the group of bradycardia pacing support, overdrive pacing and antitachycardia pacing.

21. A method according to claim 20, wherein said parasympathetic autonomic nervous system stimulation therapy is delivered in synchrony with the patient's cardiac cycle.

22. A method according to claim 20, wherein said parasympathetic autonomic nervous system stimulation therapy is electrical stimulation of the patient's vagal cervical ganglion.

23. A method according to claim 20, wherein said precursors detected in said detecting step are selected from the group including ventricular tachycardia, ventricular couplets, premature ventricular complexes, premature ventricular depolarizations, repolarization abnormalities, ST-segment elevation, ST-segment depression and late potentials.

24. A method according to claim 16, wherein said detecting step detects precursors to malignant cardiac arrhythmias and episodes of tachycardia and fibrillation and wherein said controlling step selects and directs an appropriate parasympathetic autonomic nervous system stimulation therapy in the form of electrical pulses in combination with an appropriate heart stimulation therapy selected from the group of bradycardia pacing support, overdrive pacing, antitachycardia pacing, cardioversion and defibrillation.

25. A method according to claim 24, wherein said parasympathetic autonomic nervous system stimulation therapy is delivered in synchrony with the patient's cardiac cycle.

26. A method according to claim 24, wherein said parasympathetic autonomic nervous system stimulation therapy is electrical stimulation of the patient's vagal cervical ganglion.

27. A method according to claim 24, wherein said precursors detected in said detecting step are selected from the group including ventricular tachycardia, ventricular couplets, premature ventricular complexes, premature ventricular depolarizations, repolarization abnormalities, ST-segment elevation, ST-segment depression and late potentials.

28. A method of operating an atrial defibrillator, comprising the steps of:

detecting an occurrence of atrial fibrillation, generating and delivering defibrillation stimulating pulses to the heart, generating and delivering stimulating pulses to a nerve stimulation electrode which is adapted to be placed in electrical contact with preselected nerve fibers within the patient's autonomic nervous system, and controlling said heart pulse stimulating means and said nerve fiber pulse stimulating means to direct performance of a combined atrial defibrillation and nerve stimulation therapy with respect to the patient's heart in response to said detection of atrial fibrillation.

29. A method according to claim 28, wherein said controlling step selects and directs an appropriate parasympathetic autonomic nervous system stimulation therapy in the form of repetitive brief bursts of electrical pulses delivered prior to generating atrial defibrillation therapy.

30. A method according to claim 29, wherein said parasympathetic autonomic nervous system stimulation therapy is electrical stimulation of the patient's vagal cervical ganglion.

* * * * *